United States Patent
Franceschini et al.

(10) Patent No.: US 12,135,337 B2
(45) Date of Patent: Nov. 5, 2024

(54) PROXIMITY DETECTION FOR ASSESSING SENSING PROBE ATTACHMENT STATE

(71) Applicant: THE GENERAL HOSPITAL CORPORATION, Boston, MA (US)

(72) Inventors: Maria A. Franceschini, Winchester, MA (US); Adriano Peruch, Cambridge, MA (US); Kuan Cheng Wu, Boston, MA (US); Marco Renna, Cavallino (IT)

(73) Assignee: The General Hospital Corporation, Boston, MA (US)

( * ) Notice: Subject to any disclaimer, the term of this patent is extended or adjusted under 35 U.S.C. 154(b) by 101 days.

(21) Appl. No.: 17/240,148

(22) Filed: Apr. 26, 2021

(65) Prior Publication Data
US 2021/0333308 A1    Oct. 28, 2021

Related U.S. Application Data

(60) Provisional application No. 63/015,315, filed on Apr. 24, 2020.

(51) Int. Cl.
*G01R 1/067* (2006.01)
*G01R 1/073* (2006.01)

(52) U.S. Cl.
CPC ..... *G01R 1/06794* (2013.01); *G01R 1/06766* (2013.01); *G01R 1/0735* (2013.01)

(58) Field of Classification Search
CPC ............ G01R 1/06794; G01R 1/06766; G01R 1/0735
See application file for complete search history.

(56) References Cited

U.S. PATENT DOCUMENTS

| | | | | |
|---|---|---|---|---|
| 6,937,951 B2* | 8/2005 | Gibb | ..................... | H03K 17/955 324/674 |
| 8,651,736 B2* | 2/2014 | Mullin | ................... | G01J 5/0011 374/209 |
| 2010/0308974 A1* | 12/2010 | Rowland | .............. | A61B 5/6882 340/10.4 |
| 2011/0101996 A1* | 5/2011 | Potyrailo | ............... | G01D 21/00 324/655 |

(Continued)

OTHER PUBLICATIONS

Noise-immune Capacitive Proximity Sensor System Reference Design, by Texas Instrument (Year: 2015).*

(Continued)

*Primary Examiner* — Paresh Patel
(74) *Attorney, Agent, or Firm* — Quarles & Brady LLP

(57) ABSTRACT

A sensor assembly and sensing method is provided for proximity detection for assessing an attachment state of a sensing probe with respect to a subject. A probe is coupled to an electronic probe controller. The probe includes a proximity sensor having a passive energy storing circuit element, and a biological sensor receptacle configured to receive a biological sensor for sensing a biological characteristic of an object. The electronic probe controller excites a circuit network incorporating the proximity sensor with an excitation signal and determines a characteristic of the circuit network that is excited by the excitation signal. The electronic probe controller further generates a proximity indication indicating whether the probe is attached to the object based on the characteristic of the circuit network.

20 Claims, 15 Drawing Sheets

(56) References Cited

U.S. PATENT DOCUMENTS

| | | | | |
|---|---|---|---|---|
| 2013/0106441 A1* | 5/2013 | Yilmaz | ................ | G06F 3/0445 324/658 |
| 2014/0095102 A1* | 4/2014 | Potyrailo | ............... | G01R 27/28 324/603 |
| 2015/0054495 A1* | 2/2015 | Lem | ................... | G01R 1/06794 417/413.2 |

OTHER PUBLICATIONS

Hu, X. and Yang, W., Planar capacitive sensors—designs and applications, School of Electrical and Electronic Engineering, The University of Manchester, Manchester, UK, (2010), pp. 24-39, vol. 30, No. 1, Emerald Group Publishing Limited.

Texas Instruments, FDC2x1x EMI-Resistant 28-Bit Capacitance-to-Digital Converter for Proximity and Level Sensing Applications, www.ti.com, (Jun. 2015). pp. 1-62.

Texas Instruments, Capacitive Frost or Ice Detection Reference Design—Resolution of < 1 mm, Temperature Drift < 0.25%, www.ti.com, (Sep. 2017). pp. 1-33.

Texas Instruments, Quantifying Ice and Frost Buildup Using Capacitive Sensors, www.ti.com, (Dec. 2017). pp. 1-3.

Texas Instruments, FDC2212 2-Ch, 28-bit, capacitance to digital converter, FDC2122 data sheet, product information and support, www.ti.com, (2021). pp. 1-5.

Toa, Mubina, Common Inductive and Capacitive Sensing Applications, Application Report, www.ti.com, (2020). pp. 1-16. Texas Instruments Incorporated.

Wang, David, Capacitive Sensing: Ins and Outs of Active Shielding, Application Report, www.ti.com, (Feb. 2015). pp. 1-13. Texas Instruments Incorporated.

Wang, David, Capacitive Proximity Sensing Using the FDC1004, Application Report, www.ti.com, (Apr. 2015). pp. 1-10. Texas Instruments Incorporated.

Yu, Yibo, Capacitive proximity Sensing Using FDC2x1y, Application Report, www.ti.com, (Oct. 2017). pp. 1-7. Texas Instruments Incorporated.

\* cited by examiner

PROXIMITY DETECTION FOR ASSESSING SENSING PROBE ATTACHMENT STATE

CROSS-REFERENCE TO RELATED APPLICATIONS

The present application is based on and claims priority from U.S. Patent Application Ser. No. 63/015,315, filed on Apr. 24, 2020, the entire disclosure of which is incorporated herein by reference.

FEDERALLY SPONSORED RESEARCH

This invention was made with government support under R01HD091067-01A1 awarded by National Institutes of Health. The government has certain rights in the invention.

BACKGROUND

Noninvasive biological sensors, also referred to as biomedical sensors, are used for monitoring biological characteristics of a subject (e.g., a human patient). The noninvasive biological sensor may be placed on the skin of the subject to perform the monitoring. In some instances, a gel or other agent is provided between the sensor and the skin to improve adherence of the sensor to the skin. Example noninvasive biological sensors include optical sensors, such as pulse oximeter sensors, hearth rate variability sensors, diffuse optical spectroscopy sensors, near-infrared spectroscopy (NIRS) sensors, diffuse correlation spectroscopy (DCS) sensors, and cerebral oximeter sensors, and may also include other wearable biosensors that use light, ultrasound, or electromagnetic fields. These noninvasive biological sensors have various applications, including cerebral and muscular oximetry, diagnosis of osteoarticular diseases, in-vivo molecular imaging, monitoring of cerebral cortex activity, detecting oxygenated/deoxygenated hemoglobin concentrations and variations, detecting blood flow (BF), monitoring of noninvasive blood pressure and intracranial pressure, as well as others.

SUMMARY OF THE INVENTION

During the course of monitoring with noninvasive biological sensors, a subject may move or shift, or an adhesive may lose adherence to the skin, and cause the sensor to detach (partially or fully) from the skin of the subject. Such detachments can cause sensing errors (e.g., inaccurate or invalid data), and may be difficult or time consuming to detect through a review of the sensor data that is generated. The potential for detachments may increase with the length of time that a subject is monitored, as well as with the age, muscular control, or temperament of the subject. Additionally, in some cases, the biological sensors include a laser source to inject light (i.e., photons) and a photo detector to sense the emitted light from the area injected with the light. In some of these biological sensors, it is desirable to cease light emission when the sensor is detached from the subject to prevent emission of light in unintended directions (e.g., towards an eye of the subject). In some wearable devices performing intermittent measurements, it is desirable to perform a reading when the contact with the skin is optimal to prevent inaccurate readings.

Accordingly, for these and other reasons, new systems, methods, and apparatuses for proximity detection for assessing an attachment state of a sensing probe with respect to a subject are desirable.

In one embodiment, a sensor assembly is provided that includes a probe and an electronic probe controller that is coupled to the probe. The probe includes a proximity sensor having a passive energy storing circuit element, and a biological sensor receptacle configured to receive a biological sensor for sensing a biological characteristic of an object. The electronic probe controller is configured to: excite a circuit network incorporating the proximity sensor with an excitation signal, determine a characteristic of the circuit network that is excited by the excitation signal, and generate a proximity indication indicating a probe attachment state based on the characteristic of the circuit network.

In another embodiment, a method is provided that includes exciting a circuit network incorporating a proximity sensor with an excitation signal. The proximity sensor has a passive energy storing circuit element and is incorporated into a probe with a biological sensor receptacle configured to receive a biological sensor for sensing a biological characteristic of an object. The method further includes determining a characteristic of the circuit network that is excited by the excitation signal. The method also includes generating a proximity indication indicating a probe attachment state based on the characteristic of the circuit network

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

DETAILED DESCRIPTION

One or more embodiments are described and illustrated in the following description and accompanying drawings. These embodiments are not limited to the specific details provided herein and may be modified in various ways. Furthermore, other embodiments may exist that are not described herein. Also, functions performed by multiple components may be consolidated and performed by a single component. Similarly, the functions described herein as being performed by one component may be performed by multiple components in a distributed manner. Additionally, a component described as performing particular functionality may also perform additional functionality not described herein. For example, a device or structure that is "configured" in a certain way is configured in at least that way, but may also be configured in ways that are not listed.

As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "comprising," "including," "containing," "having," and variations thereof herein is meant to encompass the items listed thereafter and equivalents thereof as well as additional items. Additionally, the terms "connected" and "coupled" are used broadly and encompass both direct and indirect connecting and coupling, and may refer to physical or electrical connections or couplings. Furthermore, the phase "and/or" used with two or more items is intended to cover the items individually and both items together. For example, "a and/or b" is intended to cover: a; b; and a and b.

Figure 1A:
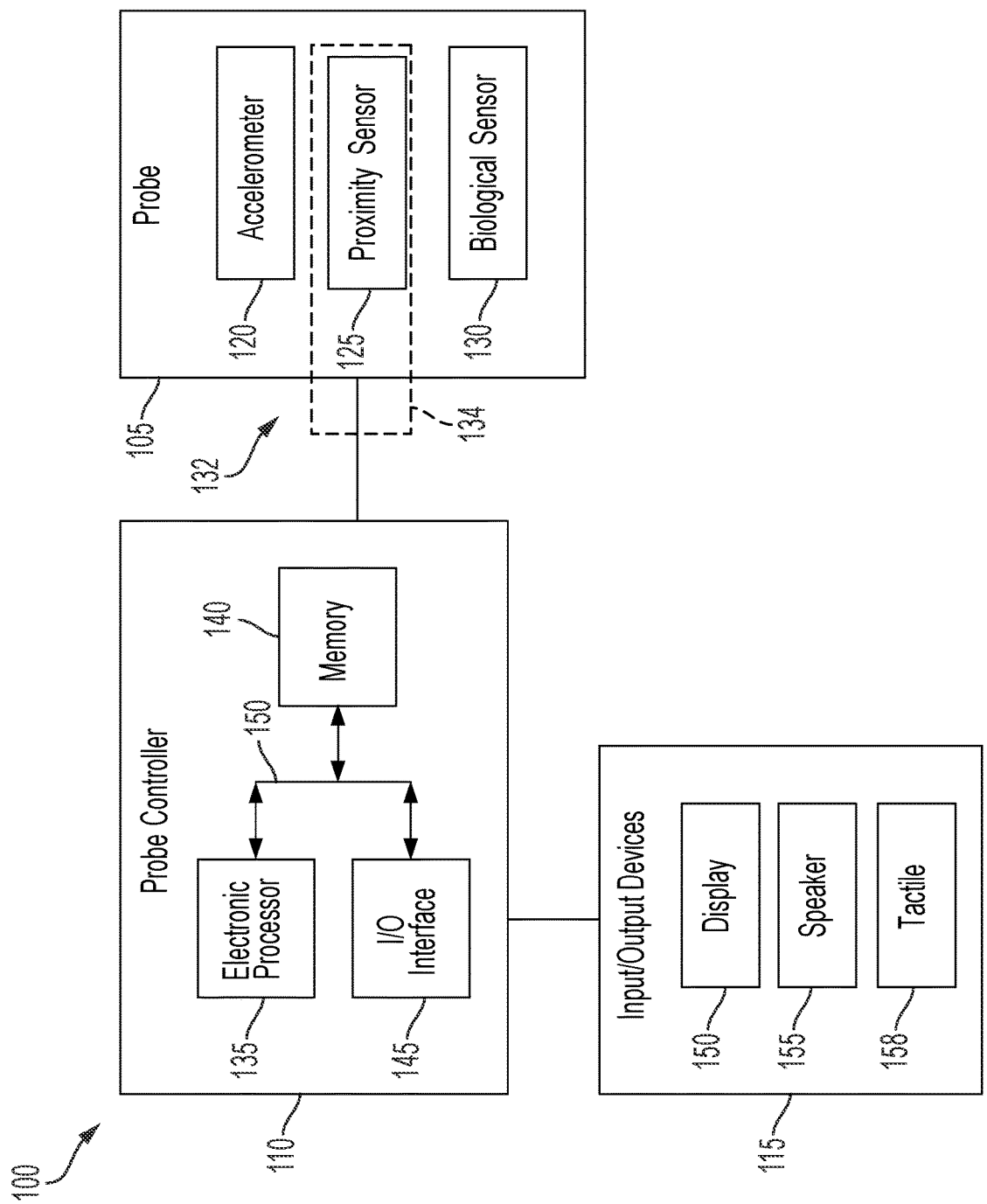
FIGS. 1A-B illustrate a sensor assembly according to some embodiments.

FIG. 1A illustrates a sensor assembly 100 including a sensing probe 105 (herein probe 105), a probe controller 110, and input/output devices 115. The probe 105 includes a motion sensor 120, a proximity sensor 125, and a biological sensor 130 and is connected to the probe controller 110 by a communication circuit 132. The motion sensor 120 is, for example, a three-axis MEMS accelerometer that is configured to sense motion in three dimensions and provide an output indicative of the same. In some examples, when the motion sensor 120 includes an accelerometer, the accelerometer has a range of plus or minus two times the acceleration due to gravity (i.e., +2 g to −2 g) and a 1.6 kilohertz (kHz) bandwidth. However, in other examples, the range and bandwidth is greater or less than these values. In some examples, the motion sensor 120 is gyroscope (e.g., a multi-axis gyroscope). In some examples, the motion sensor 120 includes both an accelerometer (e.g., a 3-axis MEMS accelerometer) and a gyroscope. The proximity sensor 125 is, for example, a capacitive or inductive sensor configured to sense and provide an indication of the proximity of the probe 105 to an object under measure (e.g., a human subject). The proximity sensor 125, which may also be referred to as a contact sensor, is described in further detail below. The sensor assembly 100 further includes a circuit network 134, which includes the proximity sensor 125 and a portion of the communication circuit 132, as described in further detail below.

The probe controller 110 is an electronic controller including an electronic processor 135, a memory 140, an input/output interface 145, and a communication bus 150 connecting these components. The memory 140 includes one or more of a read only memory (ROM), random access memory (RAM), or other non-transitory computer-readable media. The electronic processor 135 is configured to, among other things, receive instructions and data from the memory 140 and execute the instructions to, for example, carry out the functionality of the probe controller 110 described herein, including the processes 500 of FIG. 5 and 600 of FIG. 6. Generally, the electronic processor 135 may be configured to execute control software to control the probe 105 (e.g., based on input from the input/output devices 115), receive sensor data from the probe 105, and provide output indicative of the sensor data to the input/output devices 115. In some embodiments, the electronic processor 135 is a processing circuit implemented entirely in hardware circuitry (e.g., an application specific circuit) such that the functions of the electronic processor 135 (and the probe controller 110) described herein are performed by this hardware circuitry, rather than by processing software instructions retrieved from a memory.

The input/output interface 145 includes input and output interface elements that enable the electronic processor 135 to communicate with and control the other components of the probe assembly 100, including the user input/output devices 115. In some embodiments, the input/output interface 145 enables wireless and/or wired communication according to one or more known protocols (e.g., Wi-Fi, Bluetooth, USB, etc.). For example, the input/output interface 145 includes wired or wireless interface circuitry, such as antennas, wired ports, and transceivers for transmitting and receiving signals using antennas and/or wired ports.

Although the probe controller 110 is illustrated as a single unit, in some embodiments, one or more components of the probe controller 110 is remote from the other components, is a distributed component, or a combination thereof. For example, in some embodiments, the memory 140 includes local memory co-located with the electronic processor 135 as well as remote memory located off-site and, for example, connected to the electronic processor 135 by one or more networks (e.g., a local area network or another wide area network such as the Internet). Similarly, in some embodiments, the electronic processor 135 includes one or more local microprocessors and, in other embodiments, the electronic processor 135 is a distributed processing system including a combination of one or more local microprocessors and remote processors (e.g., cloud computing).

The input/output devices 115 include one or more devices enabling a user to interact with the probe assembly 100. As illustrated, the user input/output devices 115 includes a display 150, a speaker 155, and a tactile device 158 (e.g., a motor providing vibration or other tactile feedback) for indicating alerts, settings, sensor data, and the like generated by the probe controller 110 (e.g., based on sensor data obtained via the probe 105). In some examples, one or more of the input/output devices 115 receive input, for example, to control activation of or settings for the probe controller 110 and/or the probe 105. For example, the display 145 may be a touch screen display that is configured to receive input from a user. In some embodiments, one or more other input/output devices 115 are provided in addition to or instead of the elements shown in FIG. 1A. For example, the input/output devices 115 may include one or more further displays, touchscreens, touchscreen displays, keyboards, mice, pushbuttons, dials, pedals, and the like.

In some embodiments, the electronic processor 135, memory 140, and I/O interface 145 of the probe controller 110 include multiple processors, memories, and interface components, respectively. Further, these multiple components may be selectively grouped together, for example, into sub-controllers of the probe controller 110 and/or onto one or more circuit boards. For example, with reference to FIG. 1B, the electronic processor 135, memory 140, and I/O interface 145 take the form of two sub-controllers: a proximity controller 160 and a biological sensor controller 165. The proximity controller 160 and the biological sensor controller 165 divide the functionality of the probe controller 110, with the proximity controller 160 generally implementing the functions related to the motion sensor 120 and proximity sensor 125 and the biological sensor controller 165 generally implementing the functions related to the biological sensor 130. Each of the proximity controller 160 and the biological sensor controller 165 include a respective electronic processor, memory, I/O interface, and communication bus that are similar to the electronic processor 135, memory 140, I/O interface 145, and communication bus 150 described above. The electronic processors of the controllers 160 and 165 may collectively be considered the electronic processor 135 of the probe controller 100; the memories of the controllers 160 and 165 may collectively be considered the memory 140; and the I/O interfaces of the controllers 160 and 165 may collectively be considered the I/O interface 145.

Figure 1B:
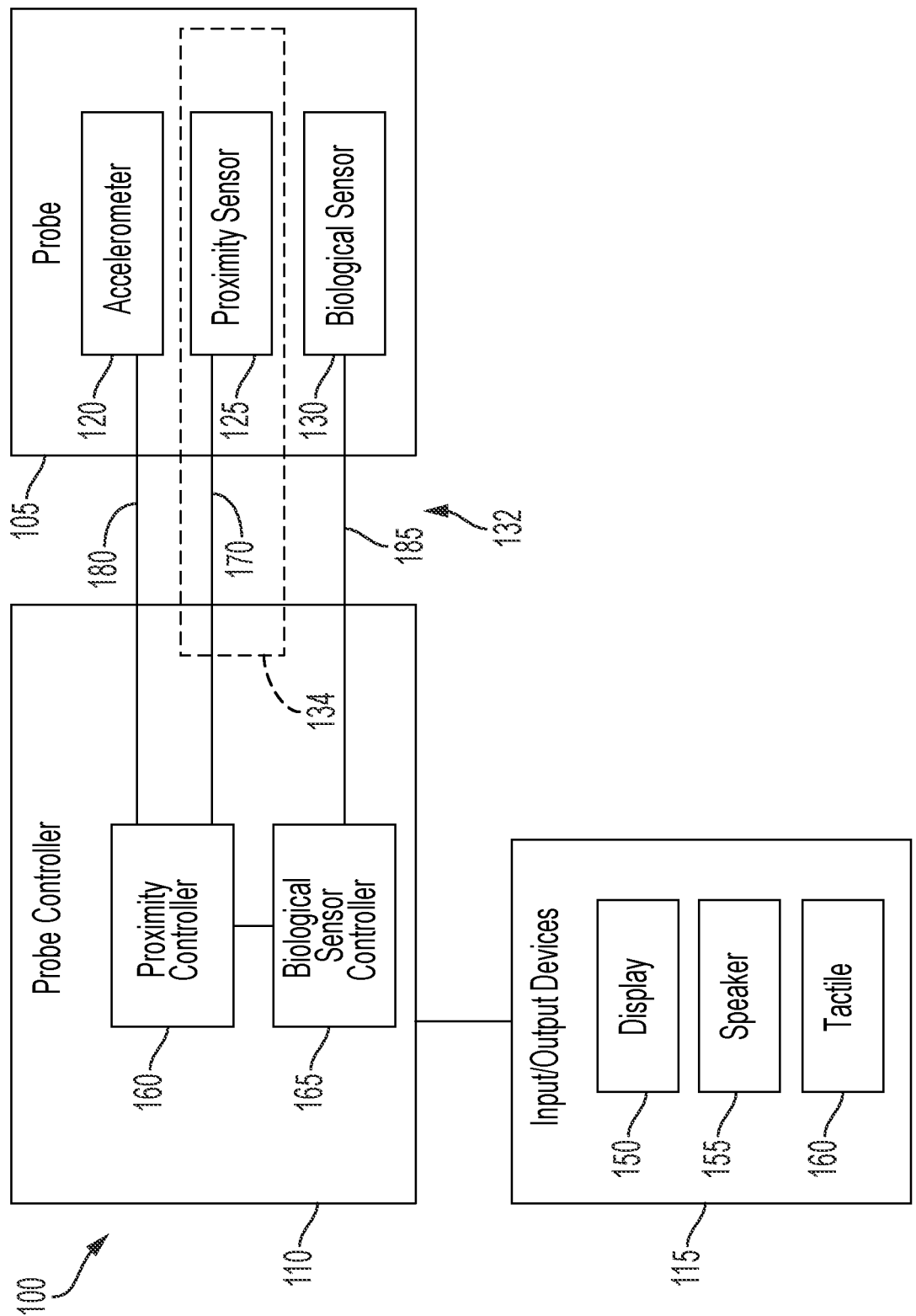

With continued reference to FIG. 1B, in some embodiments, the communication circuit 132, which connects the probe 105 and the probe controller 110, includes circuit elements 170 that, together with the proximity sensor 125, form the circuit network 134. The circuit elements 170 may include one or more discrete circuit elements (e.g., resistors, capacitors, inductors) and/or intrinsic resistive, capacitive, and/or inductive properties. The circuit network 134 is described in further detail below with respect to the process 600 and examples provided in FIGS. 7A-E. The communication circuit 132 further includes one or more motion sensor wires 180 connecting the motion sensor 120 to the proximity controller 160 and one or more biological sensor wires 185 connecting the biological sensor 130 with the biological sensor controller 165. In some embodiments, the description of the communication circuit 132 with respect to FIG. 1B similarly applies to the communication circuit 132 of FIG. 1A.

Figure 2A:
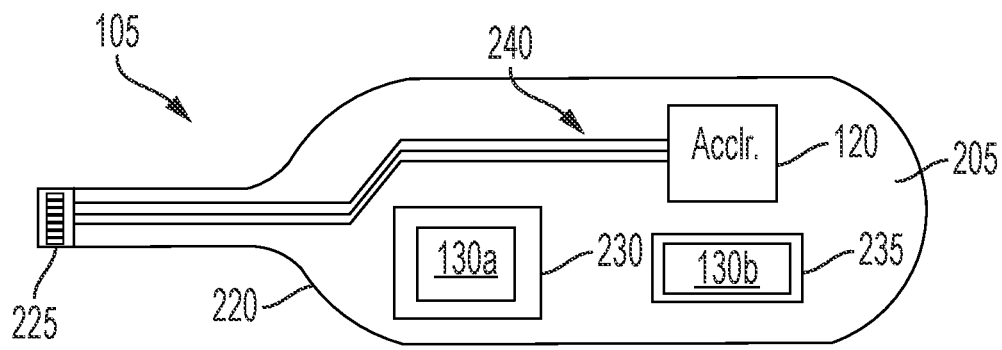
FIG. 2A illustrates a back-side view of a probe of the sensor assembly of FIGS. 1A-B, according to some embodiments.
Figure 2B:
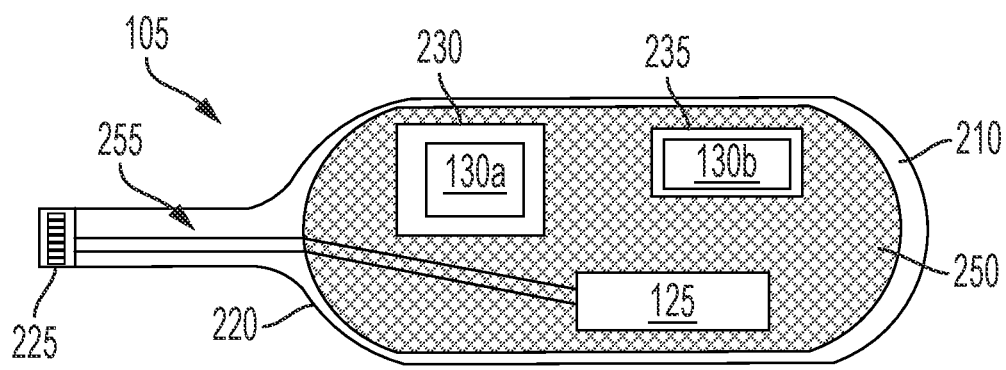
FIG. 2B illustrates a sensing-side view of a probe of the sensor assembly of FIGS. 1A-B, according to some embodiments.
Figure 2C:
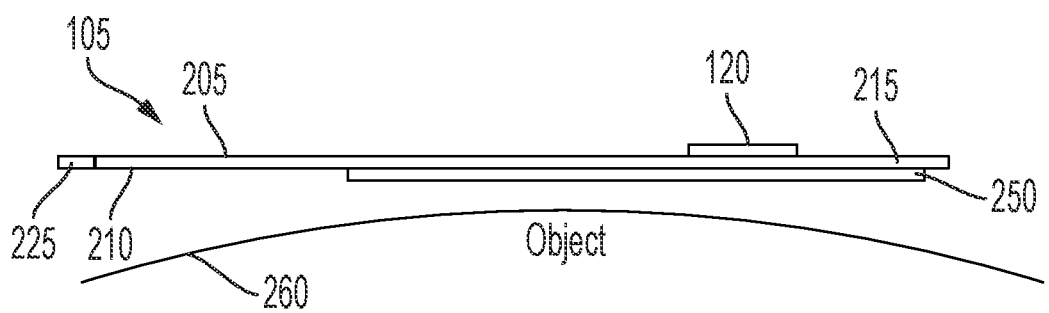
FIG. 2C illustrates a profile view of a probe of the sensor assembly of FIGS. 1A-B, according to some embodiments.

Turning to FIGS. 2A-C, multiple views of an example of the probe 105 are provided. FIG. 2A illustrates a back-side 205 of the probe 105, FIG. 2B illustrates a sensing (front) side 210 of the probe 105, and FIG. 2C illustrates a profile-side 215 of the probe 105. As shown in FIG. 2A, the probe 105 includes a substrate 220 having a terminal block 225, biological sensor receptacles 230 and 235 (herein receptacles 230 and 235), and motion sensor traces 240. The motion sensor traces 240 connect the terminal block 225 to the motion sensor 120 mounted on the substrate 220. The receptacles 230 and 235 receive the biological sensor 130, which includes two sub-components 130a and 130b. The sub-components 130a and 130b may be, for example, a laser source and a photo detector, respectively. In another embodiment, the sub-component 130a may include both a laser source and a photo detector and the sub-component 130b may include a separate photo detector.

The receptacles 230 and 235 receive and physically secure the biological sensor 130 to the probe 105, but do not provide an electrical connection between the biological sensor 130 and the probe 105 (e.g., terminals of the biological sensor 130 are not connected to conductive traces on the substrate 220). Rather, the biological sensor 130 has independently run cables to connect to the probe controller 110. The receptacles 230 and 235 include, for example, through-holes in the substrate 220 sized to fit and retain the biological sensor 130. For example, the biological sensor 130 (e.g., each of the sub components 130a and 130b) may have flexible flanges that can securely couple to the perimeter of the receptacles 230 and 235. For example, with reference to FIGS. 3A-C, which illustrate an example of the probe 105, the sub-components 130a and 130b have flanges 305 (FIG. 3B) and independent cables 310 for connecting to the probe controller 110.

Returning to FIGS. 2A-C, the terminal block 225 ultimately connects the motion sensor 120 and the proximity sensor 125 to the probe controller 110. For example, the terminal block 225 may be connected via a flexible cable (e.g., a ribbon cable) to the probe controller 110.

Although the biological sensor 130 is illustrated as having two sub-components, in some embodiments, the biological sensor 130 is a single unit or has more than two sub-components. In some embodiments, the probe 105 includes fewer or more biological sensor receptacles than illustrated in FIGS. 2A-C to receive the biological sensor 130 (e.g., as a single unit or as more than two sub-components). Additionally, in some embodiments, the biological sensor 130 is surface-mounted to the substrate 220 and electrically connected to the terminal block 225 via conductive traces on the substrate 220 for ultimate connection to the probe controller 110.

Turning to FIG. 2B, the sensing side 210 includes a surface area 250 on which the proximity sensor 125 is provided. In FIG. 2B, the proximity sensor 125 is illustrated as a rectangle on the surface area 250; however, the proximity sensor 125 may take various forms and shapes, and may take up different portions of the surface area 250, as described in further detail herein. Additionally, the proximity sensor 125 is connected to the terminal block 225 via conductive traces 255. Although two conductive traces 255 are illustrated, in some embodiments, fewer or more conductive traces are provided. For example, in some embodiments, only a single conductive trace 255 is provided to connect the proximity sensor 125 to the terminal block 225.

Turning to FIG. 2C, an object 260 (e.g., a human subject) is provided adjacent to the sensing side 210 of the probe 105. As illustrated, the object 260 includes a curved surface (e.g., skin) where the probe 105 is to engage for measurements. However, the shape and form of the object 260 may vary. For example, the object 260 may be flat, may be curved, or may have a combination of various flat and curved portions. In some examples, the object 260 is a forehead region of a human. In some embodiments, the substrate 220 is flexible and can conform to a curved or otherwise non-flat surface of the object 260. For example, with reference to FIG. 3C, the probe 105 is shown in a flexed or curved state. In some examples, the substrate 220 is a flexible printed circuit board made of a polyimide material. In some embodiments, the substrate 220 is rigid and does not flex to conform to a curved surface. The rigid substrate 220 may be flat, curved, or have a combination of flat and curved portions.

In some embodiments, the probe 105 includes shielding, which may be passive or active. Passive shielding includes a grounded conductor placed near the sensor 125 in the direction in which shielding is desired. The grounded conductor shields the proximity sensor 125 from influence by objects on the other side of the ground conductor relative to the proximity sensor 125. In other words, the proximity sensor 125 may have little to no sensitivity beyond the interface with the grounded conductor (passive shield). Active shielding includes a conductor that is placed near the proximity sensor 125 in the direction in which shielding is desired. The conductor may then be actively driven by the probe controller 110 in counterphase to the sensing signal of the proximity sensor 125 (e.g., the oscillating signal 760 described below with respect to FIGS. 7A-7D). The conductor shields the proximity sensor 125 from influence by objects on the other side of the conductor relative to the proximity sensor 125. In other words, the proximity sensor 125 may have little to no sensitivity beyond the interface with the conductor (active shield).

In some embodiments, passive shielding is provided on the probe 105 by grounding the copper on the back-plane (e.g., on the back side 205) of the substrate 220 (see FIG. 2A). This passive shielding avoids false attachment sensing due to unwanted or incidental additional contact on the probe 105 (e.g., by a human subject touching the probe 105).

Figure 3A:
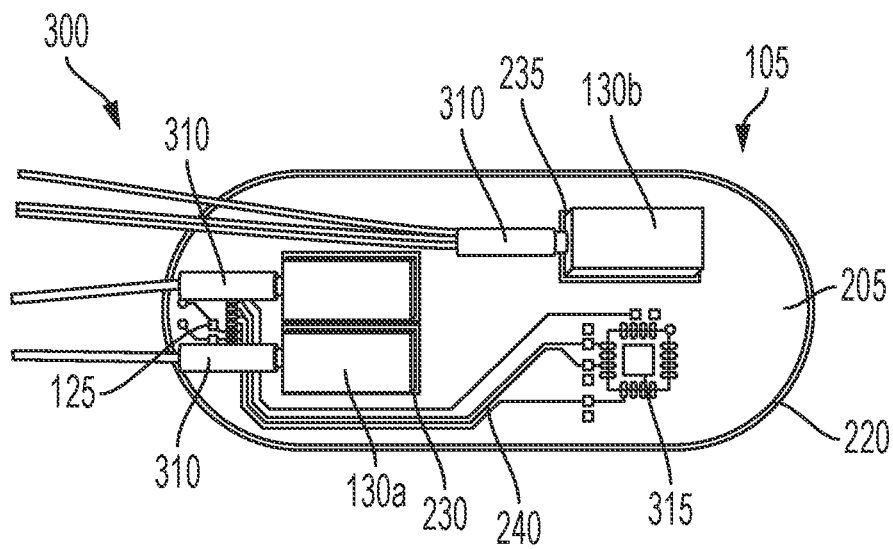
FIG. 3A illustrates a back-side view of a probe of the sensor assembly of FIGS. 1A-B, according to some embodiments.
Figure 3B:
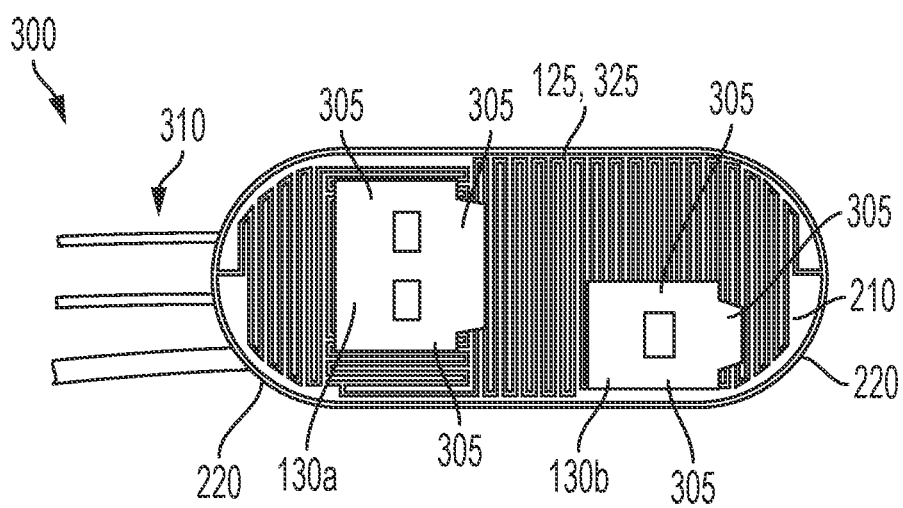
FIG. 3B illustrates a sensing-side view of a probe of the sensor assembly of FIGS. 1A-B, according to some embodiments.
Figure 3C:
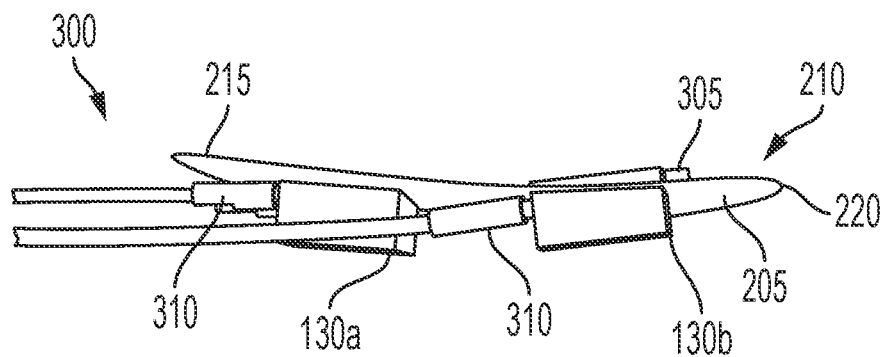
FIG. 3C illustrates a profile view of a probe of the sensor assembly of FIGS. 1A-B, according to some embodiments.

Turning to FIGS. 3A-C, a probe 300, which is an example of the probe 105, is illustrated. Element numbers of FIGS. 1A, 1B, 2A-C are reused in FIGS. 3A-C to indicate like parts. FIG. 3A illustrates a back-side 205 of the probe 300, FIG. 3B illustrates a sensing (front) side 210 of the probe 300, and FIG. 3C illustrates a profile-side 215 of the probe 300. As previously noted, the biological sensor subcomponents 130a and 130b have flanges 305 to secure the subcomponents 130a and 130b within the receptacles 230 and 235. Additionally, the biological sensor subcomponents 130a and 130b are connected to the probe controller 110 via cables 310, rather than conductive traces on the substrate 220. FIG. 3A also illustrates a surface mounting pad 315 to which the motion sensor 120 may be surface-mounted. FIG. 3B further illustrates an example of the proximity sensor 125 in the form of a winding or serpentine conductor 325 that serves as a first conductor of a capacitor.

FIGS. 4A-e illustrate probes 405a-e, respectively, which are each an example of the probe 105. Accordingly, element numbers of FIGS. 1A, 1B, 2A-C are reused in FIGS. 4A-E to indicate like parts. Each of the probes 405a-e has a different example of the proximity sensor 125 on the sensing side 210.

Figure 4A:
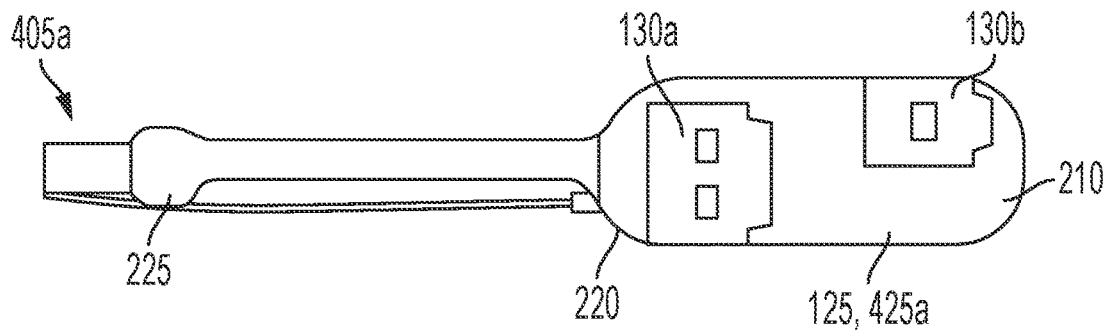
FIGS. 4A-E illustrate example probes of the sensor assembly of FIGS. 1A-B, each probe having a different proximity sensors.

FIG. 4A illustrates an isolated pad conductor 425a as the proximity sensor 125 of the probe 405a. The isolated pad conductor 425a is a single flat electrode that occupies a portion or majority of the sensing side 210, excluding the area occupied by the biological sensor 130. The conductor 425a serves as a first conductor of a capacitor of the proximity sensor 125. When the probe 405a is attached to an object (see, e.g., the object 260 of FIG. 2C), the object serves as a second conductor of the capacitor of the proximity sensor 125. Accordingly, when the probe 405a is attached to another object, the capacitance of the proximity sensor 125 increases. Likewise, when the probe 405a detached from the object, the capacitance of the proximity sensor 125 decreases. As explained in further detail below, the capacitance of the proximity sensor 125 of the probe 405a can be measured. Thus, the proximity sensor 125 of the probe 405a is configured to serve as a capacitive proximity sensor that indicates to the probe controller 110 the proximity of the probe 405a to an object (e.g., whether the probe 405a is attached or detached from the object).

Figure 4B:
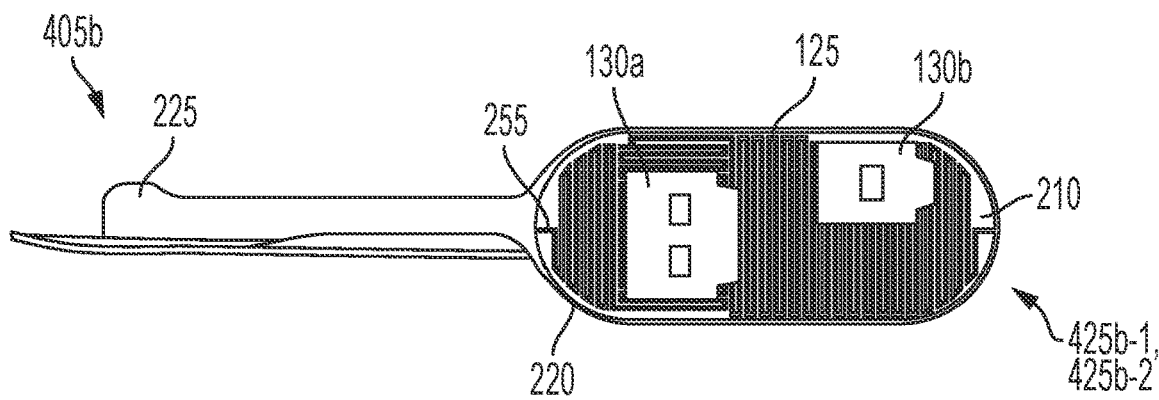

FIG. 4B illustrates interdigital conductors 425b-1 and 425b-2 (collectively, interdigital conductors 425b) as the proximity sensor 125 of the probe 405b. Each interdigital conductor 425b-1 and 425b-2 are isolated conductive traces that together occupy a portion or majority of the sensing side 210, excluding the area occupied by the biological sensor 130. In some embodiments, each interdigital conductor 425b-1 and 425b-2 is a winding or serpentine conductor that respectively serve as first and second conductors to form a capacitor of the proximity sensor 125. When the probe 405b is attached to another object (see, e.g., the object 260 of FIG. 2C), the object changes the dielectric constant of the capacitor of the proximity sensor 125, and the capacitance of the proximity sensor 125 increases. Likewise, when the probe 405b detaches from the object, the capacitance of the proximity sensor 125 decreases. In some embodiments, the interdigital conductors 425b-1 and 425b-2 may be electrically connected (i.e., shorted together), resulting in the conductors 425b-1 and 425b-2 together serving as a first conductor of a capacitor of the proximity sensor 125 (that functions similar to the proximity sensor 125 of the probe 405a). Thus, the proximity sensor 125 of the probe 405b is also configured to serve as a capacitive proximity sensor that indicates to the probe controller 110 the proximity of the probe 405b to an object (e.g., whether the probe 405b is attached or detached from the object).

Figure 4C:
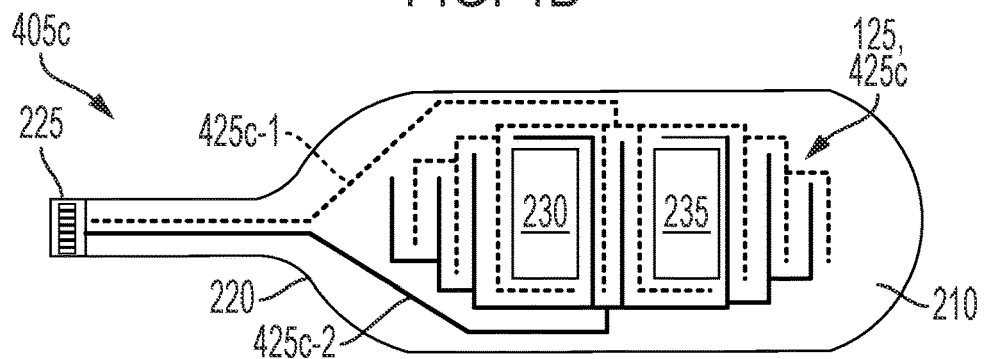

FIG. 4C illustrates interdigital conductors 425c-1 and 425c-2 (collectively, interdigital conductors 425c) as the proximity sensor 125 of the probe 405c. Each interdigital conductor 425c-1 and 425c-2 are isolated conductive traces that together occupy a portion or majority of the sensing side 210, excluding the area occupied by the biological sensor 130. In some embodiments, each interdigital conductor 425c-1 and 425c-2 is a winding or serpentine conductor that respectively serve as first and second conductors to form a capacitor of the proximity sensor 125. When the probe 405c is attached to another object (see, e.g., the object 260 of FIG. 2C), the object changes the dielectric constant of the capacitor of the proximity sensor 125, and the capacitance of the proximity sensor 125 increases. Likewise, when the probe 405c detaches from the object, the capacitance of the proximity sensor 125 decreases. In other embodiments, each interdigital conductor 425c-1 and 425c-2 is a winding or serpentine conductor that serves as a respective first conductor of a first and second capacitor of the proximity sensor 125. When the probe 405c is attached to another object (see, e.g., the object 260 of FIG. 2C), the object serves as a second conductor of the capacitors of the proximity sensor 125 and the capacitance of the proximity sensor 125 increases. Likewise, when the probe 405c detaches from the object, the capacitance of the proximity sensor 125 decreases. Thus, the proximity sensor 125 of the probe 405c is also configured to serve as a capacitive proximity sensor that indicates to the probe controller 110 the proximity of the probe 405c to an object (e.g., whether the probe 405c is attached or detached from the object).

Figure 4D:
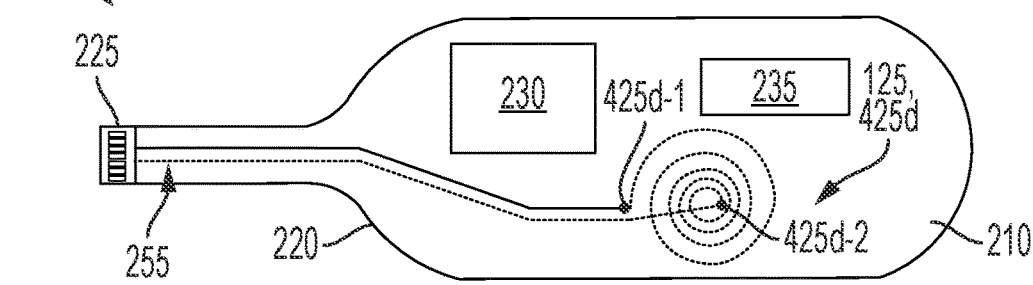

FIG. 4D illustrates an inductor 425d as the proximity sensor 125 of the probe 405d. The inductor 425d is a conductive trace or wire having a spiral shape with one connection point 425d-1 on an outer portion of the spiral and a second connection point 425d-2 on an inner portion of the spiral. The connection points 425d-1 and 425d-2 are connected via the conductive traces 255 to the terminal block 225. Although the shape of the inductor 425*d* is a single, round or circular spiral, in other embodiments, another shape may be used. For example, FIGS. 4F-4O illustrate alternate inductor shapes that may be used as the inductor 425*d* that include rectangular or octagonal spirals, coils, or sets of coils. The inductor 425*d* occupies a portion or majority of the sensing side 210, excluding the area occupied by the biological sensor 130. When the probe 405*d* is attached to another object (see, e.g., the object 260 of FIG. 2C) that is conductive (e.g., metals or wet skin), the object decreases the inductance of the proximity sensor 125. Likewise, when the probe 405*d* detaches from the object, the inductance of the proximity sensor 125 increases. Thus, the proximity sensor 125 of the probe 405*d* is configured to serve as an inductive proximity sensor that indicates to the probe controller 110 the proximity of the probe 405*d* to an object (e.g., whether the probe 405*d* is attached or detached from the object). For non-conductive objects, the change in inductance of the inductor 425*d* may be small or negligible, but the inductor 425*d* may act as a capacitor such as previously described with respect to FIGS. 4A-C (e.g., an attached or proximate object increases the capacitance of the inductor 425*d*).

Figure 4E:
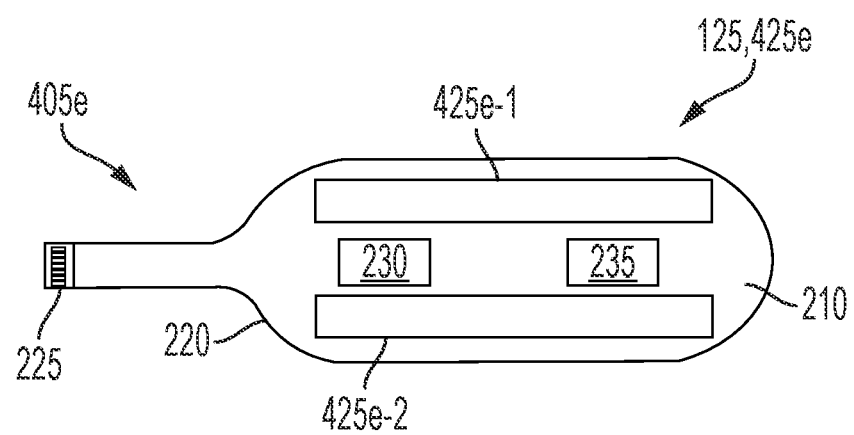
Figure 4F:
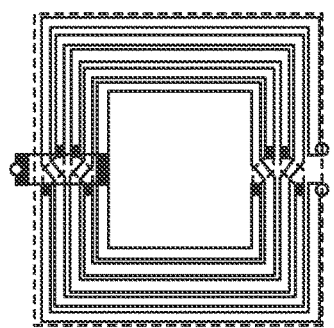
FIGS. 4F-O illustrate example inductor configurations for the proximity sensor of the probe of FIG. 4D.
Figure 4G:
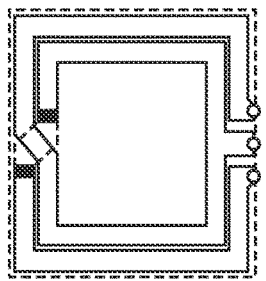
Figure 4H:
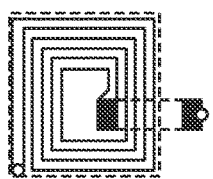
Figure 4I:
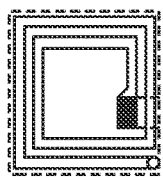
Figure 4L:
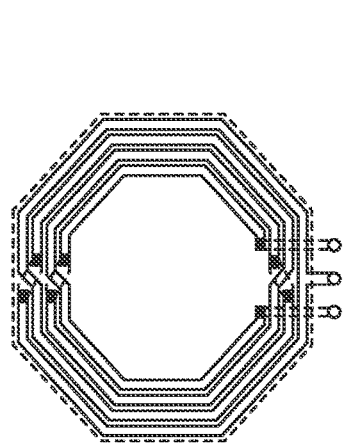
Figure 4K:
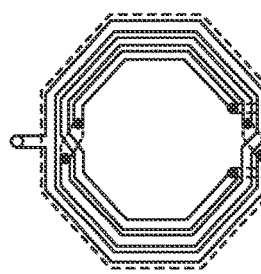
Figure 4J:
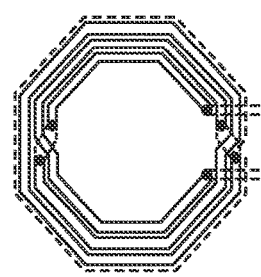
Figure 4O:
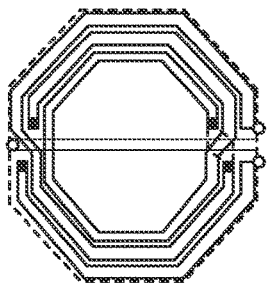
Figure 4N:
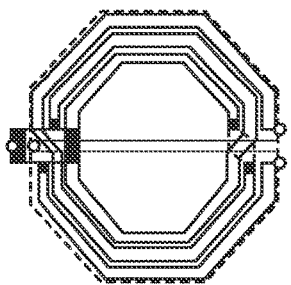
Figure 4M:
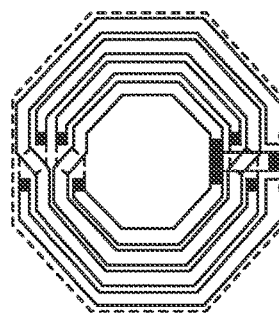

FIG. 4E illustrates two plate conductors 425*e*-1 and 425*e*-2 (collectively, plate conductors 425*e*) as the proximity sensor 125 of the probe 405*e*. Each plate conductor 425*e*-1 and 425*e*-2 is an isolated conductor and, together, they occupy a portion or majority of the sensing side 210, excluding the area occupied by the biological sensor 130. In some embodiments, each plate conductor 425*e*-1 and 425*e*-2 is a conductor that serves as a respective first conductor of a first and second capacitor of the proximity sensor 125. When the probe 405*e* is attached to another object (see, e.g., the object 260 of FIG. 2C), the object serves as a second conductor of the capacitors of the proximity sensor 125 and the capacitance of the proximity sensor 125 increases. Likewise, when the probe 405*e* detaches from the object, the capacitance of the proximity sensor 125 decreases. Thus, the proximity sensor 125 of the probe 405*e* is also configured to serve as a capacitive proximity sensor that indicates to the probe controller 110 the proximity of the probe 405*e* to an object (e.g., whether the probe 405*e* is attached or detached from the object).

In some embodiments, a protective dialectic coating (e.g., a thin polymer layer) is applied over the top of the proximity sensor 125 (and, thus, the proximity sensors 425*a-e*) on the sensing side 210 to provide galvanic insulation between the probe 105 and the object to be sensed.

The probes 405*a-e* have a generally oval shape with a length that is longer than a width. In some examples, one or more of the probes 405*a-e* have a length that is between 44 millimeters (mm) and 36.5 mm and a width that is between 19 mm and 15.2 mm. In other embodiments, the length and/or width is greater or less than this range of values. In some embodiments, the probes 405*a-e* have a shape other than an oval, such as circular or rectangular.

Figure 5:
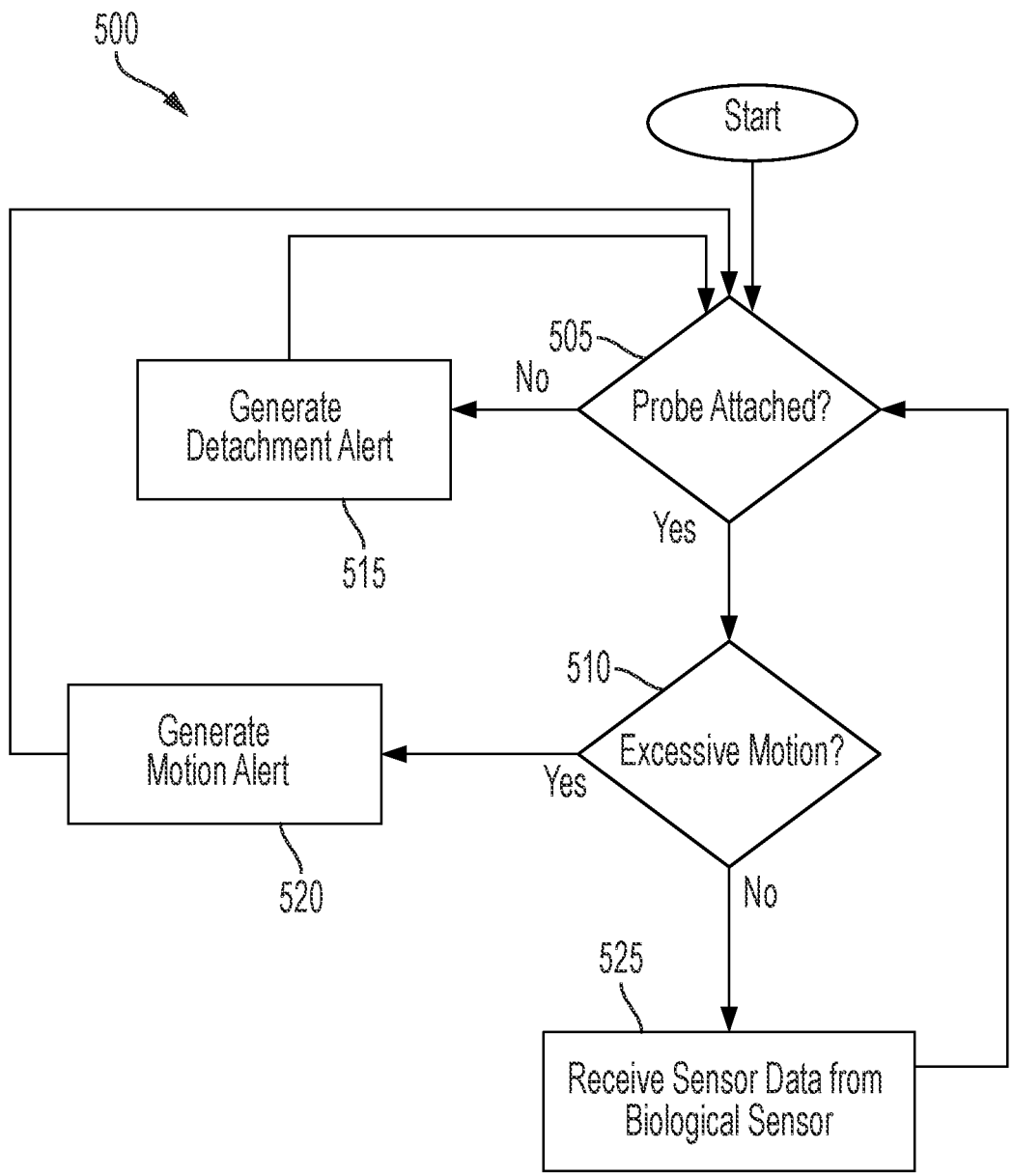
FIG. 5 illustrates a process for sensing using the sensor assembly of FIGS. 1A-B, according to some embodiments.

FIG. 5 illustrates a process 500 for sensing using the sensor assembly 100 including the probe 105. Although the process 500 is described as being carried out by the sensor assembly 100, in some embodiments, the process 500 may be implemented by another sensor assembly. Additionally, although the blocks of the process 500 are illustrated in a particular order, in some embodiments, one or more of the blocks may be executed partially or entirely in parallel, may be executed in a different order than illustrated in FIG. 5, or may be bypassed. As described above, the probe 105 of the sensor assembly 100 may take the form of one of the probes 105 of FIGS. 2A-C, 300 of FIGS. 3A-C, 405*a-e* of FIGS. 4A-E, or another form.

In block 505, the probe controller 110 determines whether the probe 105 is attached to an object to be monitored. The probe controller 110 determines whether the probe 105 is attached to the object (or has an attachment quality level above a quality threshold) based on proximity data received from the proximity sensor 125, as described in further detail with respect to the process 600 of FIG. 6.

When, in block 505, the probe controller 110 determines that the probe 105 is not attached to the object, the probe controller 110 generates a detachment alert (block 515). Generating the detachment alert may include the probe controller 110 transmitting a detachment alert signal to one or more of the input/output devices 115 (e.g., the display 150, the speaker 155, or the tactile device 158) to indicate to an operator or user of the detachment. For example, in response to receipt of the detachment alert signal, the display 150 may generate a visual indication that detachment occurred, the speaker 155 may generate an audible indication that detachment occurred, and/or the tactile device 158 may generate a vibration that indicates that detachment occurred. The detachment alert may indicate that the probe 105 is detached, or may more specifically indicate whether the probe 105 is partially attached, fully detached, or another attachment quality level indication.

After generating the detachment alert in block 515, the probe controller 110 returns to block 505 to again determine whether the probe 105 has been attached to the object. Accordingly, the probe controller 110 loops through steps 505 and 515 until the probe controller 110 determines that the probe 105 is attached to the object. When, in block 505, the probe controller 110 determines that the probe 105 is attached to the object, the probe controller 110 advances to block 510.

In block 510, the probe controller 110 determines whether the probe 105 is experiencing excessive motion based on motion data from the motion sensor 120. For example, the probe controller 110 receives motion data from the motion sensor 120. The motion data may include analog or digital signals indicating a measurement of motion experienced by the probe 105 in one or more dimensions (e.g., three dimensions). For example, the motion data may include three signals: a first signal indicating motion (e.g., acceleration) in the x-direction, a second signal indicating motion in the y-direction, and a third signal indicating motion in the z-direction. The probe controller 110 may compare the signals individually to respective motion thresholds or may combine the signals (e.g., a sum the absolute values indicated by each signal) and compare the combined signal to an overall motion threshold. The motion threshold(s) may be predetermined or may be set during a setup stage based on an absolute offset or percentage offset from baseline motion measurements by the motion sensor 120. In evaluating the motion data in block 510, the probe controller 110 may calculate an average of the motion signals (individually or combined) over a sliding time window (e.g., of the last 5, 10, 50, or 500 milliseconds) to reduce influence of momentary fluctuations and noise. In some embodiments, the probe controller 110 may calculate an average of the motion signals individually over a sliding time window, then sum the absolute values of the averaged signals, and then compare the sum to the motion threshold.

When the probe controller 110 determines that motion is excessive, the probe controller 110 generates a motion alert (block 520). Generating the motion alert may include the probe controller 110 transmitting the motion alert signal to one or more of the input/output devices 115 (e.g., the display 150, the speaker 155, or the tactile device 158) to indicate to an operator or user of the excessive motion. For example, in response to receipt of the motion alert signal, the display 150 may generate a visual indication that excessive motion occurred, the speaker 155 may generate an audible indication that excessive motion occurred, and/or the tactile device 158 may generate a vibration that indicates that excessive motion occurred.

When the probe controller 110 determines that motion is not excessive in block 510, the probe controller 110 proceeds to block 525. In block 525, the probe controller 110 receives sensor data from the biological sensor 130. The probe controller 110 may output the sensor data (e.g., to the input/output devices 115) and/or may store the sensor data in the memory 140 for later output (e.g., to the input/output devices 115). The sensor data may be analog signals, digital signals, or a combination of analog and digital signals, and varies dependent on the type of biological sensor 130. For example, in some embodiments, the biological sensor 130 is a DCS sensor positioned on a forehead of a patient), where the DCS sensor includes a laser source (e.g., a high-coherence laser) and two photo detectors spaced at different distances from the laser source, such as shown in the probe 300 of FIGS. 3A-3B. In this example, the sensor data may include signals from the two photo detectors indicating sensed light generated by the laser source and reflected by the patient (e.g., reflected by red blood cells). Of course, the biological sensor 130 may take various forms, as previously noted with respect to FIG. 1A. The probe controller 110 may return to block 505 to continuously assess whether the probe 105 is attached and (in block 510) whether the probe 105 is experiencing excessive motion.

When the probe controller 110 determines that the probe 105 is no longer attached (in block 505) or is experiencing excessive motion (in block 510), the probe controller 110 ceases receiving sensor data from the biological sensor 130. Ceasing reception of the sensor data may include the probe controller 110 controlling the biological sensor 130 to stop sensing (e.g., disabling an laser sources or other transmitting elements of the biological sensor 130) or may include the probe controller 110 invalidating further sensor data being sent by the biological sensor 130 or may flag the data as having artifacts. To invalidate the sensor data from the biological sensor 130, the probe controller 110 may stop outputting the sensor data sent by the biological sensor 130, may stop storing any such sensor data, and/or may mark any such sensor data as invalid in the memory 140.

In some embodiments in which the probe controller 110 includes the proximity controller 160 and biological sensor controller 165, as shown in FIG. 1B, the controllers 160 and 165 corporate to execute the blocks 505-525. For example, in block 505, the proximity controller 160 may implement the process 600 of FIG. 6 (described below) and provide the biological sensor controller 165 with a proximity indication indicating whether the probe 105 is attached to the object to be monitored. Similarly, in block 510, the proximity controller 160 may determine and indicate to the biological sensor controller 165 whether the probe 105 is experiencing excessive motion based on the motion data from the motion sensor 120 (e.g., using the above-described techniques). Further, when the biological sensor controller 165 has received an indication that the probe 105 is attached (in block 505) and has received an indication that the probe 105 is not experiencing excessive motion (in block 510), the biological sensor controller 165 may proceed to receive the sensor data from the biological sensor 130 in block 525.

After the biological sensor controller 165 begins receiving the sensor data in block 525, the probe controller 110 (i.e., the proximity controller 160 and the biological sensor controller 165 in this example) may, in parallel, return to block 505 to continuously determine whether the probe 105 is attached and, then in block 510, whether the probe 105 is experiencing excessive motion. In the event that the proximity controller 160 indicates to the biological sensor controller 165 that the probe 105 is detached (in block 505) or that the probe 105 is experiencing excessive motion (in block 510), the probe controller 110 proceeds to block 515 or 520, as the case may be, and the biological sensor controller 165 ceases receiving the sensor data that was initiated in block 525. As noted, ceasing reception of the sensor data may include one or more of the probe controller 110 controlling the biological sensor 130 to stop sensing, invalidating further sensor data being sent by the biological sensor 130, or flagging the data as having artifacts. The probe controller 110 (i.e., the proximity controller 160 and the biological sensor controller 165 in this example) may then continue to loop through blocks 505-520 until it determines that the probe 105 is attached and not experiencing excessive motion.

Figure 6:
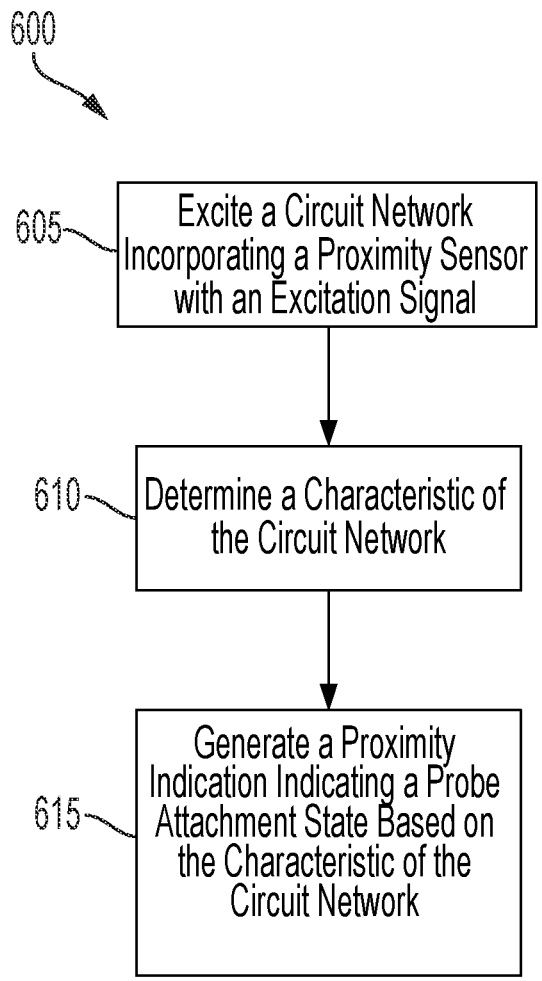
FIG. 6 illustrates a process for determining and indicating a probe attachment state, according to some embodiments.

FIG. 6 illustrates a process 600 for determining and indicating a probe attachment state for a probe with respect to an object to be monitored. The process 600 is described with respect to the sensor assembly 100; however, in some embodiments, the process 600 is implemented by another sensor assembly. Additionally, although the blocks of the process 600 are illustrated in a particular order, in some embodiments, one or more of the blocks may be executed partially or entirely in parallel, may be executed in a different order than illustrated in FIG. 6, or may be bypassed. The sensor assembly 100 executing the process 600 may include the probe 105 and the circuit network 134. The probe 105 may take the form of one of the probes 105 of FIGS. 2A-C, 300 of FIGS. 3A-C, 405a-e of FIGS. 4A-e, or another form. The circuit network 134 may take the form of one of the example circuit network configurations 710a-e of FIGS. 7A-E, respectively. Accordingly, before proceeding with a description of the process 600, a description is provided with respect to the example circuit network configurations 710a-e of FIGS. 7A-E.

FIGS. 7A-7E illustrate diagrams 700a-e including example configurations of the circuit network 134 of the sensor assembly 100 that may be used with the process 600. In each of the configurations of FIGS. 7A-D, the circuit network 134 is and may be referred to as a resonant network 710a-d, respectively. Each resonant network 710a-d includes the proximity sensor 125 and the circuit elements 170. The proximity sensor 125 of each respective resonant network 710a-d may be individually identified as one of the proximity sensors 125a-d (e.g., the proximity sensor 125 of the resonant network 710a in FIG. 7A may be referred to individually as the proximity sensor 125a). Similarly, the circuit elements 170 of each respective resonant network 710a-d may be individually identified as one of the circuit elements 715a-d). The circuit elements 715a-d include at least one capacitor 720 (also referred to as a tank capacitor $C_{TANK}$), at least one inductor 725 (also referred to as a tank inductor $L_{TANK}$), and at least one stray capacitance 730 ($C_{STRAY}$). Each stray capacitance 730 may be the stray capacitance of a conductive wire connecting the proximity sensor 125 to the probe controller 110. Generally, as the length of the conductive wire connecting the proximity sensor 125 to the probe controller 110 increases, the capacitance of the stray capacitance 730 increases. The resonant networks 710a-d further include a first node 732 and a second node 734, with the tank capacitor 720 and the tank inductor 725 being coupled between the first node 732 and the second node 734.

Each of the resonant networks 710a-d form an LC circuit that resonate at a frequency governed by their respective inductive and capacitive elements. Additionally, each of the proximity sensors 125a-d of the resonant networks 710a-d include at least one passive energy storing circuit element, such as a capacitor or an inductor. Further, the at least one passive energy storing circuit element has a variable parameter (e.g., capacitance or inductance) that varies based on whether the probe 105 incorporating the proximity sensor 125 is attached to the object to be monitored. By determining the frequency of an oscillating signal on the resonant networks 710a-d, the probe controller 110 can determine the variable parameter (capacitance or inductance) and, in turn, whether the probe 105 is attached to the object to be monitored and, in some embodiments, the quality of the attachment.

Figure 7A:
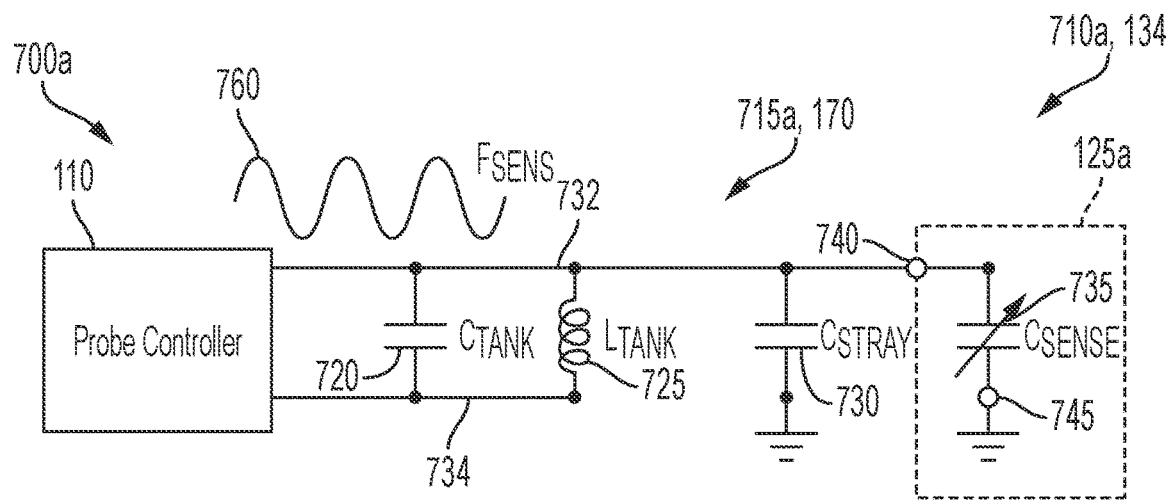
FIGS. 7A-E illustrate diagrams of example circuit networks of the sensor assembly of FIGS. 1A-B, according to some embodiments.

In FIG. 7A, the proximity sensor 125a is a capacitance sensor having a capacitance 735 ($C_{SENSE}$) with a first node 740 coupled to the first node 732 of the circuit elements 715a and a second node 745. The second node 745 is coupled to ground, as illustrated, when the proximity sensor 125a is in contact with an object. When no object is in contact with the proximity sensor 125a, the second node 745 is floating and the capacitance 735 ($C_{SENSE}$) can be seen as 0 farads. The capacitance 735 represents the at least one passive energy storing circuit element of the proximity sensor 125a. The proximity sensor 125a may be implemented by the proximity sensor 125 of the probe 405a of FIG. 4A and may also be implemented by the proximity sensor 125 of the probe 405b of FIG. 4B (when the interdigital conductors 425b-1 and 425b-2 are shorted together). Thus, in some examples, the first conductor 425a of the probe 405a of FIG. 4A is the at least one passive energy storing circuit element and provides the capacitance 735, and in some examples, the conductors 425b-1 and 425b-2 of the probe 405b of FIG. 4B are the at least one passive energy storing circuit element and provides the capacitance 735. As described with respect to the proximity sensor 125 of FIGS. 4A and 4B, when the sensing side 210 of the proximity sensor 125 attaches to the object to be monitored, the capacitance of the proximity sensor 125 increases. Likewise, when the sensing side 210 of the proximity sensor 125 detaches (partially or fully) from the object to be monitored, the capacitance of the proximity sensor 125 decreases. The capacitance 735 of the proximity sensor 125a is similar to the variable capacitance of the probe 405a and 405b. That is, the capacitance 735 ($C_{SENSE}$) is variable and increases in response to contact of a sensing side of the proximity sensor 125a with an object, such as a patient, and decreases in response to loss of contact (full or partial) with an object. For example, the capacitance 735 ($C_{SENSE}$) may equal the intrinsic capacitance of the proximity sensor 125a plus the capacitance added by an object attached to the sensing side 210 (if any) with respect to ground.

In some embodiments of the resonant network 710a, an additional wire is connected to the second node 734 and extends from the probe controller 110 and terminates at the probe 105 (e.g., at a dummy terminal of the terminal block 225 shown in FIG. 2). This additional wire, which may be represented by an additional stray capacitance 730 connected between the second node 734 and ground, compensates for the stray capacitance that may be introduced by a single long wire (e.g., connecting the nodes 732 and 740) and balances the resonant network 710a. Thus, with this additional wire, changes in the capacitance 735 may be more prominent and easier to detect when long wires are used to connect the probe 105 to the probe controller 110.

Figure 7B:
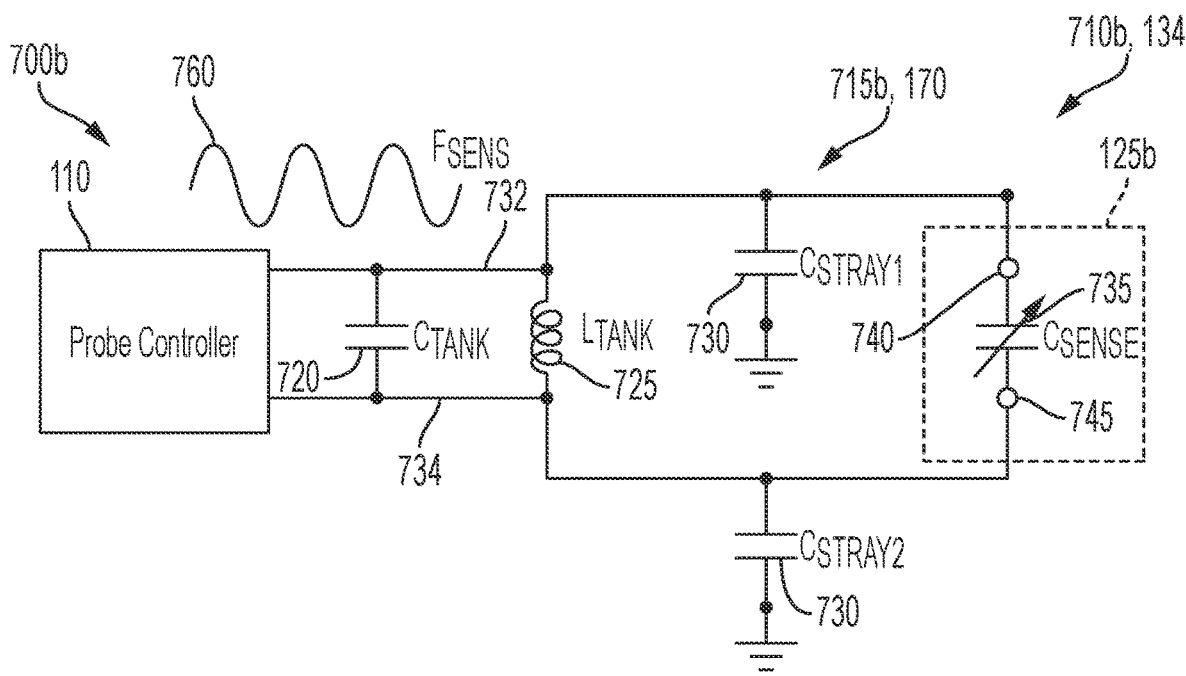

FIG. 7B illustrates the resonant network 710b, which, except for differences noted herein, is similar to the resonant network 710a and uses similar element numbering as the resonant network 710a. In the resonant network 710b, the proximity sensor 125b is also a capacitance sensor having a capacitance 735 ($C_{SENSE}$) with a first node 740 coupled to the first node 732 of the circuit elements 715a. However, a second node 745 of the capacitance 735 is coupled to the second node 734 and a further stray capacitance 730 ($C_{STRAY\ 2}$). The capacitance 735 represents the at least one passive energy storing circuit element of the proximity sensor 125 of FIG. 7B. The proximity sensor 125b may be implemented by the proximity sensor 125 of the probe 405b of FIG. 4B and also may be implemented by the proximity sensor 125 of the probe 405c of FIG. 4C. Thus, in some examples, the first conductor 425b-1 and the second conductor 425b-2 of the probe 405b of FIG. 4B are the at least one passive energy storing circuit element and provide the capacitance 735; and in some further examples, the first conductor 425c-1 and the second conductor 425c-2 of the probe 405c of FIG. 4C are the at least one passive energy storing circuit element and provide the capacitance 735. As described with respect to the proximity sensors 125 of FIGS. 4B and 4C, when the sensing side 210 of the proximity sensor 125 attaches to the object to be monitored, the capacitance of the proximity sensor 125 increases. Likewise, when the sensing side 210 of the proximity sensor 125 detaches (partially or fully) from the object to be monitored, the capacitance of the proximity sensor 125 decreases. The capacitance 735 of the proximity sensor 125b is similar to the variable capacitance of the probes 405b and 405c. That is, the capacitance 735 ($C_{SENSE}$) is variable and increases in response to contact of a sensing side of the proximity sensor 125c with an object, such as a patient, and decreases in response to loss of contact (full or partial) with an object. For example, the capacitance 735 ($C_{SENSE}$) may equal the intrinsic capacitance of the proximity sensor 125c plus the capacitance added by an object attached to the sensing side 210 (if any). The intrinsic capacitance of the proximity sensor 125c includes the capacitance of the capacitor formed by the first and second conductors (e.g., the conductors 425b-1 and 425b-2 or the conductors 425c-1 and 425c-2). The object may add capacitance to the capacitance 735 ($C_{SENSE}$) by changing the dielectric constant of the capacitor formed by the first and second conductors.

Figure 7C:
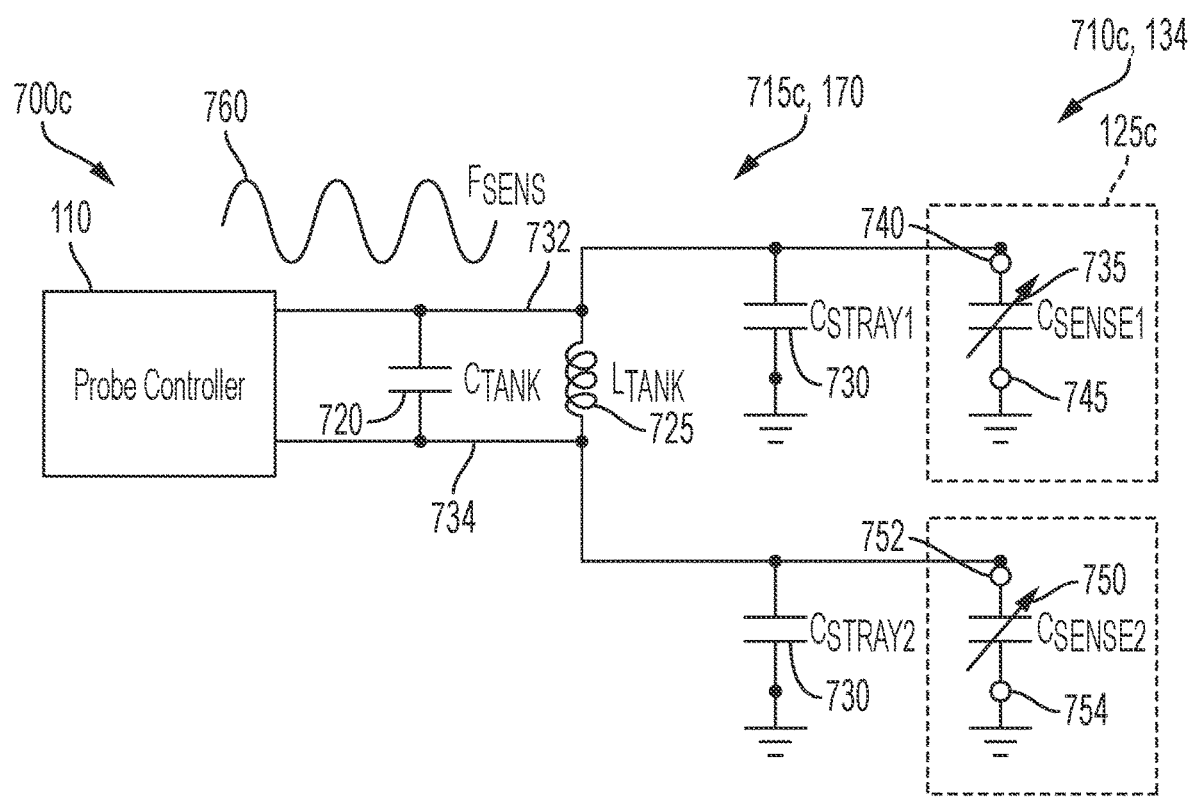

FIG. 7C illustrates the resonant network 710c, which, except for differences noted herein, is similar to the resonant network 710a and uses similar element numbering as the resonant network 710a. In the resonant network 710c, the proximity sensor 125c is also a capacitance sensor having a capacitance 735 ($C_{SENSE\ 1}$) with a first node 740 coupled to the first node 732 of the circuit elements 715c and a second node 745 coupled to ground. However, the proximity sensor 125c further includes a capacitance 750 ($C_{SENSE\ 2}$) having a first node 752 coupled to the second node 734 of the circuit elements 715c and a further stray capacitance 730 ($C_{STRAY\ 2}$) and having a second node 754 coupled to ground. The capacitances 735 and 750 represent the at least one passive energy storing circuit element of the proximity sensor 125c of FIG. 7C. The proximity sensor 125c may be implemented by the proximity sensor 125 of the probe 405c of FIG. 4C and by the proximity sensor 125 of the probe 405e. Thus, in some examples, the first conductor 425c-1 of the probe 405c of FIG. 4C is a first passive energy storing circuit element and provides the capacitance 735 and the second conductor 425c-2 of the probe 405c of FIG. 4C is a second passive energy storing circuit element and provides the capacitance 750. Additionally, in some examples, the first conductor 425e-1 of the probe 405e of FIG. 4E is a first passive energy storing circuit element and provides the capacitance 735 and the second conductor 425e-2 of the probe 405e of FIG. 4E is a second passive energy storing circuit element and provides the capacitance 750. As described with respect to the proximity sensor 125 of FIGS. 4C and 4E, when the sensing side 210 of the proximity sensor 125 attaches to the object to be monitored, the capacitance of the proximity sensor 125 increases. Likewise, when the sensing side 210 of the proximity sensor 125 detaches (partially or fully) from the object to be monitored, the capacitance of the proximity sensor 125 decreases. The capacitances 735 and 750 of the proximity sensor 125c are similar to the variable capacitance of the probe 405c and the probe 405e. That is, the capacitance 735 ($C_{SENSE\ 1}$) and the capacitance 750 ($C_{SENSE\ 2}$) are variable and increase in response to contact of a sensing side of the proximity sensor 125c with an object, such as a patient, and decrease in response to loss of contact (full or partial) with an object. For example, the capacitance 735 ($C_{SENSE\ 1}$) and the capacitance 750 ($C_{SENSE\ 2}$) may equal the intrinsic capacitance of the proximity sensor 125c plus the capacitance added by an object attached to the sensing side 210 (if any) with respect to ground.

Figure 7D:
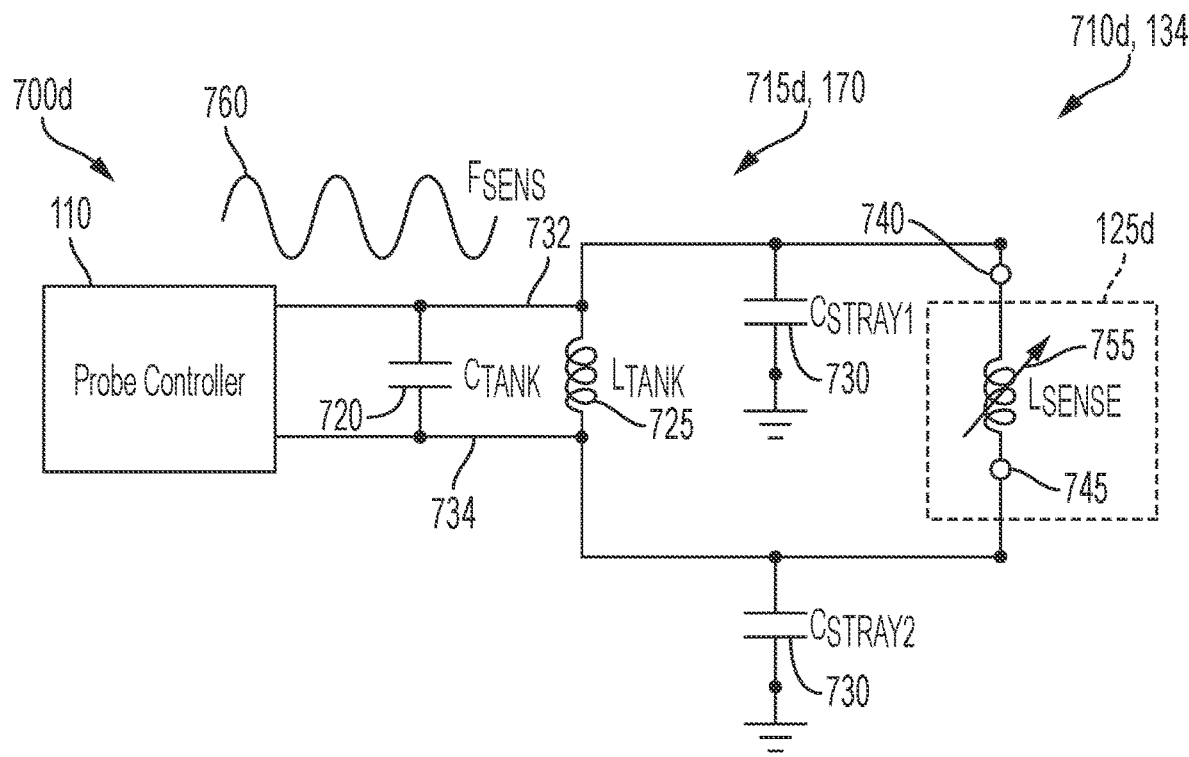

FIG. 7D illustrates the resonant network 710d, which, except for differences noted herein, is similar to the resonant network 710a and uses similar element numbering as the resonant network 710a. In the resonant network 710d, the proximity sensor 125d is an inductive sensor having an inductance 755 ($L_{SENSE}$) with a first node 740 coupled to the first node 732 of the circuit elements 715a. However, a second node 745 of the inductance 755 is coupled to the second node 734 and a further stray capacitance 730. The inductance 755 represents the at least one passive energy storing circuit element of the proximity sensor 125d of FIG. 7D. The proximity sensor 125d may be implemented by the proximity sensor 125 of the probe 405d of FIG. 4D. Thus, in some examples, the conductor 425d of the probe 405d of FIG. 4D is the at least one passive energy storing circuit element and provides the inductance 755. As described with respect to the proximity sensor 125 of FIGS. 4D, when the sensing side 210 of the proximity sensor 125 attaches to the object to be monitored, the inductance of the proximity sensor 125 decreases. Likewise, when the sensing side 210 of the proximity sensor 125 detaches (partially or fully) from the object to be monitored, the inductance of the proximity sensor 125 increases. The inductance 755 of the proximity sensor 125d is similar to the variable inductance of the probe 405d. That is, the inductance 755 ($L_{SENSE}$) is variable and decreases in response to contact of a sensing side of the proximity sensor 125d with an object, such as a patient, and increases in response to loss of contact (full or partial) with an object. For example, the inductance 755 ($L_{SENSE}$) may equal the intrinsic inductance of the proximity sensor 125d plus the inductance added by an object attached to the sensing side 210 (if any). The intrinsic inductance of the proximity sensor 125d includes the inductance of the inductor formed by the conductors 425d.

Figure 7E:
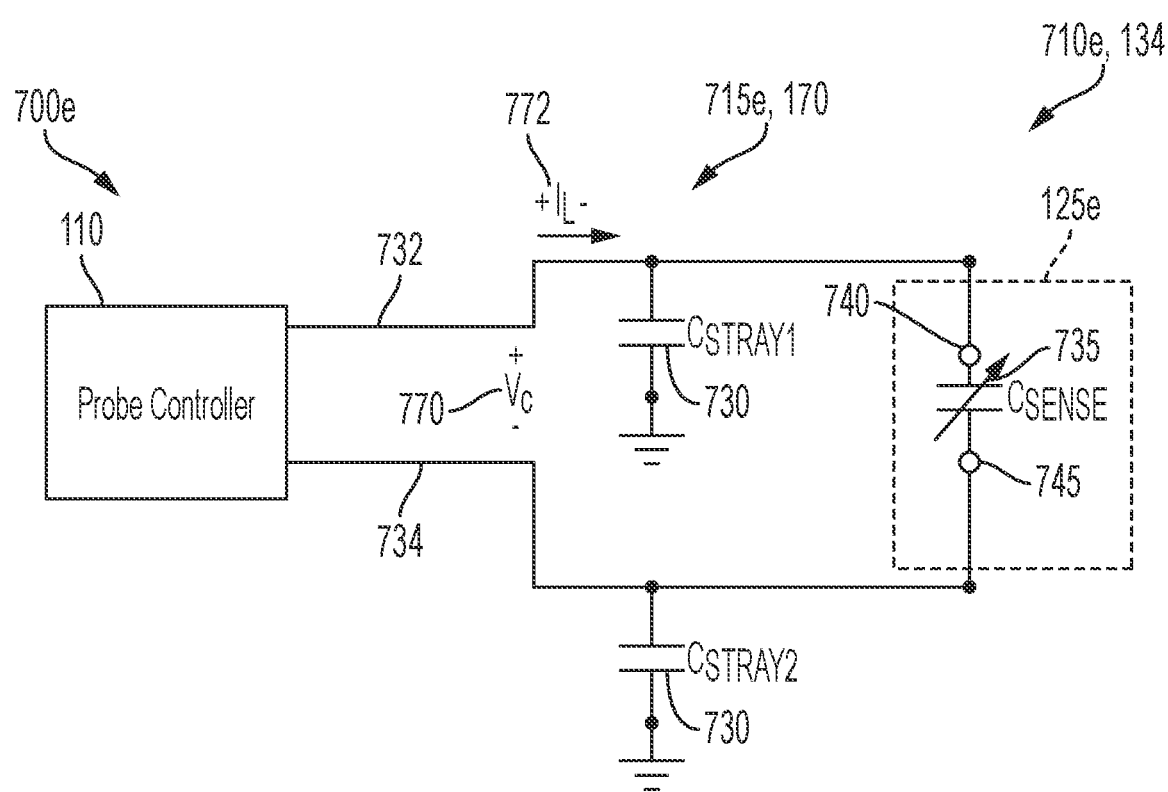

Turning to the diagram 700e of FIG. 7E, the circuit network 134 takes the form of the circuit network 710e. The circuit network 710e includes the proximity sensor 125 and the circuit elements 170. The proximity sensor 125 of the circuit network 710e may be individually identified as the proximity sensors 125e, and the circuit elements 170 of the circuit network 710e may be individually identified as the circuit elements 715e. The circuit elements 715e include at least two stray capacitances 730 ($C_{STRAY\ 1\ and\ 2}$). Each stray capacitance 730 may be the stray capacitance of a conductive wire connecting the proximity sensor 125e to the probe controller 110. The circuit network 710e further include a first node 732 and a second node 734, with the proximity sensor 125e being coupled between the first node 732 and the second node 734. The proximity sensor 125e includes at least one passive energy storing circuit element, such as a capacitor or an inductor. Further, the at least one passive energy storing circuit element has a variable parameter (e.g., capacitance or inductance) that varies based on whether the probe 105 incorporating the proximity sensor 125e is attached to the object to be monitored. By determining the charge time of the circuit network 710e, the probe controller 110 can determine the variable parameter (capacitance or inductance) and, in turn, whether the probe 105 is attached to the object to be monitored and, in some embodiments, the quality of the attachment. The proximity sensor 125e may be implemented by, for example, each of the proximity sensors 125 of the probes 405b, 405c, and 405d of FIGS. 4B, 4C, and 4D. The charge times for circuit networks of the probes 405a and 405e could also be used in a similar manner to determine the capacitance of the circuit network and, in turn, whether the probe 405a and 405e are attached to the object and a quality of the attachment.

Returning now to FIG. 6, the process 600 for determining and indicating a probe attachment state for a probe with respect to an object to be monitored is described.

In block 605, the probe controller 110 excites the circuit network 134 incorporating the proximity sensor 125 with an excitation signal. For example, with reference to FIG. 7A in which the circuit network 134 takes the form of the resonant network 710a, the probe controller 110 generates an excitation signal (e.g., an alternating current (AC) signal at the nodes 732 and 734) that excites the resonant network 710a incorporating the proximity sensor 125a of the probe 105. Accordingly, the excitation signal may be a periodic signal. To generate the excitation signal, the probe controller 110 may include an oscillator circuit including a tank having a resistor, inductor, capacitor (RLC) network and a negative gain stage to compensate for the resistive components of the tank and sustain the oscillation. Thus, the resonant network 710a forms an LC circuit that resonates. When excited by the excitation signal, an oscillating signal 760 of the resonant network 710a oscillates at a frequency ($F_{SENS}$) corresponding to its inductive ($L_{TANK}$) and capacitive elements ($C_{TANK}$, $C_{STRAY}$, and $C_{SENSE}$). In some embodiments, the frequency FSENS when the probe 105 is not attached to an object is about 4 MHz; however, this is merely an example, as the frequency varies based on the various capacitances and inductances of the network. By altering the inductive and capacitive components of the tank (i.e., $L_{TANK}$ and $C_{TANK}$), the resolution and measurement range may be varied, with a higher frequency generally resulting in a higher resolution and shorter range. The oscillating signal 760 may be a voltage signal or a current signal. When the circuit network takes the form of one of the resonant networks 710b-d of FIGS. 7B-D, the probe controller 110 generates an excitation signal in a similar manner. As a result, in these resonant networks 710b-d, the oscillating signal 760 oscillates at the frequency ($F_{SENS}$) corresponding to the inductive and capacitive elements of each respective resonant network 710b-d. With reference to FIG. 7E in which the circuit network 134 takes the form of the circuit network 710e including a capacitance 735, the probe controller 110 generates an excitation signal (e.g., a direct current (DC) constant current signal across the nodes 732 and 734) that excites the circuit network 710e incorporating the proximity sensor 125e of the probe 105. When excited by the excitation signal, the voltage signal 770 of the circuit network 710e rises as the capacitive elements of the circuit network 710e (e.g., $C_{STRAY}$ and $C_{SENSE}$) are charged by the excitation signal. In some embodiments of the circuit network 710e, an inductor is provided as the passive element of the proximity detector 125e, rather than a capacitor. In such embodiments, the probe controller 110 generates an excitation signal (e.g., a direct current (DC) constant voltage signal across the nodes 732 and 734) that excites the circuit network 710e incorporating the proximity sensor 125e of the probe 105. When excited by the excitation signal, a current signal 772 ($I_L$) of the circuit network 710e increases as the inductor of the proximity sensor 125 is charged by the excitation signal.

Returning to FIG. 6, in block 610, the probe controller 110 determines a characteristic of the circuit network 134. The characteristic is, for example, a capacitance or an inductance of the circuit network 134. The capacitance of the circuit network 134 may be represented by, for example, the present value or an amount of change of (i) a total capacitance of the circuit network 134 ($C_{TOT}$), (ii) a capacitance of the proximity sensor 125 ($C_{SENSE}$), (iii) a frequency of an oscillating signal of the circuit network 134 (which varies based on $C_{SENSE}$ and, thus, serves as a proxy thereof), or (iv) a charge time for the circuit network 134. The inductance of the circuit network 134 may be represented by, for example, the present value or an amount of change of (i) a total inductance of the circuit network 134 ($L_{TOT}$), (ii) an inductance of the proximity sensor 125 ($L_{SENSE}$), or (iii) a frequency of an oscillating signal of the circuit network 134 (which varies based on $L_{SENSE}$ and, thus, serves as a proxy thereof).

In some examples of block 610, with reference to FIG. 7A, the probe controller 110 determines a frequency ($F_{SENS}$) of the oscillating signal 760 on the resonant network 710a. For example, the probe controller 110 may (i) include a sensor (e.g., a current or voltage sensor) to detect peaks, valleys, or zero-crossings of the oscillating signal 760, (ii) measure the time between successive peaks, valleys, or zero-crossings (respectively) of the oscillating signal ($T_{period}$), and (iii) then calculate the inverse of $T_{period}$ (i.e., $F_{SENS} = 1/T_{period}$). The probe controller 110 may then use the frequency ($F_{SENS}$) as a proxy for the total capacitance of the resonant network 710a ($C_{TOT}$) or of the proximity sensor 125a ($C_{SENSE}$), or may calculate these values. For example, the probe controller 110 can solve the following equation for the total capacitance ($C_{TOT}$) and use the measured frequency ($F_{SENS}$) and known inductor value ($L_{TANK}$) to calculate the total capacitance of the resonant network 710a.

$$F_{SENS} = \frac{1}{2\pi\sqrt{L_{TANK} \times C_{TOT}}}$$

The probe controller 110 may use the total capacitance $C_{TOT}$ as the characteristic of the circuit network 134 or may use the following equation with the calculated $C_{TOT}$ and known values for $C_{TANK}$, and $C_{STRAY}$ to calculate $C_{SENSE}$ and use the capacitance $C_{SENSE}$ as the characteristic of the circuit network 134.

$$C_{TOT} = C_{TANK} + C_{STRAY} + C_{SENSE}$$

In some embodiments, the probe controller 110 may calculate a change in the frequency ($\Delta F_{SENS}$), a change in the total capacitance ($\Delta C_{TOT}$), or a change in the capacitance of the proximity sensor 125 ($\Delta C_{SENSE}$) as the characteristic. For example, the probe controller 110 may subtract the currently determined frequency ($F_{SENS}$), total capacitance ($C_{TOT}$), or capacitance of the proximity sensor 125 ($C_{SENSE}$) from a respective previous or baseline value of these measurements (e.g., $F_{SENS\_PREVIOUS}$, $C_{TOT\_PREVIOUS}$, or $C_{SENSE\_PREVIOUS}$). For example, the probe controller 110 may calculate these values using the following equations:

$$\Delta F_{SENS} = |F_{SENS\_PREVIOUS} - F_{SENS}|$$

$$\Delta C_{SENSE} = |C_{SENSE\_PREVIOUS} - C_{SENSE}|$$

$$\Delta C_{TOT} = |C_{TOT\_PREVIOUS} - C_{TOT}|$$

In further examples of block 610, with reference to FIGS. 7B-D, the probe controller 110 may determine a frequency ($F_{SENS}$) of the oscillating signal 760 on the respective resonant network 710b-d using a similar technique as described with respect to FIG. 7A. The probe controller 110 may then use the frequency ($F_{SENS}$) as a proxy for the capacitance of the resonant network 710b-c ($C_{TOT}$), as a proxy for the capacitance of the proximity sensor 125b-c ($C_{SENSE}$), as a proxy for the inductance of the resonant network 710d ($L_{TOT}$), as a proxy for the inductance of the proximity sensor 125d ($L_{SENSE}$), or may calculate these values. The probe controller 110 may calculate these values using similar equations as noted above with respect to FIG. 7A, except that the equations may be modified to account for the different circuit layouts of the various resonant networks 710b-d in FIGS. 7B-D. Additionally, as noted with respect to FIG. 7A, in some embodiments, the probe controller 110 may calculate a change in the frequency ($\Delta F_{SENS}$), a change in the total capacitance ($\Delta C_{TOT}$), or a change in the capacitance of the proximity sensor 125 ($\Delta C_{SENSE}$) as the characteristic for the respective resonant network 710b-d. Similarly, in some embodiments, the probe controller 110 may calculate a change in the total inductance ($\Delta L_{TOT}$), or a change in the inductance of the proximity sensor 125d ($\Delta L_{SENSE}$) as the characteristic for the respective resonant network 710b-d.

In further examples of block 610, with reference to FIG. 7E, the probe controller 110 may determine a charge time ($T_{CHARGE}$) for the voltage signal 770 ($V_C$) on the circuit network 710e to reach a charged level. For example, the probe controller 110 may include a voltage sensor that senses the voltage signal 770 ($V_C$) and a timer circuit that indicates the elapsed time (i.e., the charge time $T_{CHARGE}$) between the voltage signal 770 crossing an initial threshold and reaching a charged threshold during the course of charging by the excitation signal.

The probe controller 110 may then use the charge time ($T_{CHARGE}$) as a proxy for the capacitance of the circuit network 710e or of the proximity sensor 125 ($C_{SENSE}$), or may calculate these values using the charge time ($T_{CHARGE}$). For example, the probe controller 110 can solve the following equation for the total capacitance ($C_{TOT}$) and use the sensed voltage signal 770 ($V_C$) and measured charge time ($T_{CHARGE}$) to calculate the total capacitance of the circuit network 134.

$$V_C(t) = \frac{1}{C_{TOT}} \times t$$

The probe controller 110 may use the total capacitance $C_{TOT}$ as the characteristic of the circuit network 134 or may subtract the capacitance due to the $C_{STRAY}$ components from the total capacitance $C_{TOT}$ to calculate $C_{SENSE}$, and use the capacitance $C_{SENSE}$ as the characteristic of the circuit network 134. Additionally, similar to examples noted with respect to FIGS. 7A-D, in some embodiments, the probe controller 110 may calculate a change in the charge time ($T_{CHARGE}$), a change in the total capacitance ($\Delta C_{TOT}$), or a change in the capacitance of the proximity sensor 125 ($\Delta C_{SENSE}$) as the characteristic for the circuit network 710e by subtracting the presently determined value from a previously determined value for each respective parameter.

In some embodiments of the circuit network 710e, an inductor is provided as the passive element of the proximity detector 125e, rather than a capacitor. In such embodiments, the probe controller 110 the probe controller 110 may determine a charge time ($T_{CHARGE}$) for the current signal 772 ($I_L$) on the circuit network 710e to increase above a certain level. For example, the probe controller 110 may include a current sensor that senses the current signal 772 ($I_L$) and a timer circuit that indicates the elapsed time (i.e., the charge time $T_{CHARGE}$) between the current signal 772 ($I_L$) crossing an initial threshold and reaching a charged threshold during the course of charging by the excitation signal.

In block 615, the probe controller 110 generates a proximity indication that indicates a probe attachment state of the probe 105 based on the characteristic of the circuit network 134. For example, the probe attachment state may indicate that (i) the probe 105 is detached from the object (e.g., not in contact with the object), or (ii) that the probe 105 is attached to the object (e.g., in contact with the object). In other words, in some embodiments, the proximity indication is a binary assessment (i.e., attached or detached). Although the proximity indication may indicate that the probe 105 is detached from the object, this indication may be understood to be an assessment of the quality of the contact and the corresponding ability of the probe 105 to monitor the object. Accordingly, even though a portion of the probe 105 may be touching the object (e.g., a portion of the sensing side 210 or the back side 205), the proximity indication may indicate that the probe 105 is detached from the object when the attachment is only partial or of a non-sensing portion of the probe 105. In some embodiments, the probe attachment state may be an attachment level indicator indicating a quality of attachment of the probe 105 to the object. For example, the probe controller 110 may map the characteristic of the circuit network (determined in block 610) to an attachment quality level selected from two or more attachment quality levels (e.g., great quality, good quality, poor quality) or to a value in another quality scale (e.g., a value between 1 and 100 or between 1 and 10). Generally, for a capacitive proximity sensor, the greater the capacitance, the better the attachment quality level, and for an inductive proximity sensor, the lower the inductance, the better the attachment quality level.

In some embodiments, to generate the proximity indication in block 615, the probe controller 110 determines whether the characteristic (e.g., capacitance or inductance) of the particular circuit network 710a-e has changed above a threshold amount, and generates the proximity indication in response to determining whether the characteristic has changed above the threshold amount. In some embodiments, the characteristic of the resonant networks 710a-c for the process 600 is capacitance, the characteristic of the resonant network 710d for the process 600 is inductance, and the characteristic of the circuit network 710e for the process 600 is capacitance.

For example, with reference to FIG. 7A, in some embodiments, to generate the proximity indication in block 615, the probe controller 110 compares the capacitance of the resonant network 710a to a threshold amount. As noted with respect to block 610, the capacitance of the resonant network 710a for purposes of the process 600 is represented by, for example, the present value or an amount of change of the total capacitance of the resonant network 710a ($C_{TOT}$), capacitance of the proximity sensor 125a ($C_{SENSE}$), or frequency of an oscillating signal of the resonant network 710a (which varies based on $C_{SENSE}$ and, thus, serves as a proxy thereof). When the comparison indicates that the capacitance of the resonant network 710a has increased more than a threshold amount, the probe controller 110 generates a proximity indication indicating that the probe 105 has become attached to the object to be monitored. When the comparison indicates that the capacitance of the resonant network 710a has decreased more than a threshold amount, the probe controller 110 generates a proximity indication indicating that the probe 105 has become detached from the object to be monitored. When the comparison indicates that the capacitance of the resonant network 710a has not increased or decreased more than a threshold amount, the probe controller 110 determines that the attachment state of the probe 105 (e.g., attached to or detached from the object) has not changed, and generates a proximity indication indicating a previous attachment state of the probe 105 (whether attached or detached, as the case may be). In some embodiments, the probe controller 110 may presume that the process 600 begins with the probe 105 in a detached state. In other embodiments, the probe controller 110 may presume that the process 600 begins with the probe in an attached state.

With reference to FIG. 7B, in some embodiments, to generate the proximity indication in block 615, the probe controller 110 compares the capacitance of the resonant network 710b to a threshold amount. As noted with respect to block 610, the capacitance of the resonant network 710b for purposes of the process 600 is represented by, for example, the present value or an amount of change of the total capacitance of the resonant network 710b ($C_{TOT}$), capacitance of the proximity sensor 125b ($C_{SENSE}$), or frequency of an oscillating signal of the resonant network 710b (which varies based on $C_{SENSE}$ and, thus, serves as a proxy thereof). When the comparison indicates that the capacitance of the resonant network 710b has increased more than a threshold amount, the probe controller 110 generates a proximity indication indicating that the probe 105 has become attached to the object to be monitored. When the comparison indicates that the capacitance of the resonant network 710b has decreased more than a threshold amount, the probe controller 110 generates a proximity indication indicating that the probe 105 has become detached from the object to be monitored. When the comparison indicates that the capacitance of the resonant network 710b has not increased or decreased more than a threshold amount, the probe controller 110 determines that the attachment state of the probe 105 (e.g., attached to or detached from the object) has not changed, and generates a proximity indication indicating a previous attachment state of the probe 105 (whether attached or detached, as the case may be).

With reference to FIG. 7C, in some embodiments, to generate the proximity indication in block 615, the probe controller 110 compares the capacitance of the resonant network 710c to a threshold amount. As noted with respect to block 610, the capacitance of the resonant network 710c for purposes of the process 600 is represented by, for example, the present value or an amount of change of the total capacitance of the resonant network 710c ($C_{TOT}$), capacitance of the proximity sensor 125c ($C_{SENSE}$), or frequency of an oscillating signal of the resonant network 710c (which varies based on $C_{SENSE}$ and, thus, serves as a proxy thereof). When the comparison indicates that the capacitance of the resonant network 710c has increased more than a threshold amount, the probe controller 110 generates a proximity indication indicating that the probe 105 has become attached to the object to be monitored. When the comparison indicates that the capacitance of the resonant network 710c has decreased more than a threshold amount, the probe controller 110 generates a proximity indication indicating that the probe 105 has become detached from the object to be monitored. When the comparison indicates that the capacitance of the resonant network 710c has not increased or decreased more than a threshold amount, the probe controller 110 determines that the attachment state of the probe 105 (e.g., attached to or detached from the object) has not changed, and generates a proximity indication indicating a previous attachment state of the probe 105 (whether attached or detached, as the case may be).

With reference to FIG. 7D, in some embodiments, to generate the proximity indication in block 615, the probe controller 110 compares the inductance of the resonant network 710d to a threshold amount. As noted with respect to block 610, the inductance of the resonant network 710d for purposes of the process 600 is represented by, for example, the present value or an amount of change of the total inductance of the resonant network 710d ($L_{TOT}$), inductance of the proximity sensor 125d ($L_{SENSE}$), or frequency of an oscillating signal of the resonant network 710d (which varies based on $L_{SENSE}$ and, thus, serves as a proxy thereof). When the comparison indicates that the inductance of the resonant network 710d has decreased more than a threshold amount, the probe controller 110 generates a proximity indication indicating that the probe 105 has become attached to the object to be monitored. When the comparison indicates that the inductance of the resonant network 710d has increased more than a threshold amount, the probe controller 110 generates a proximity indication indicating that the probe 105 has become detached from the object to be monitored. When the comparison indicates that the inductance of the resonant network 710d has not increased or decreased more than a threshold amount, the probe controller 110 determines that the attachment state of the probe 105 (e.g., attached to or detached from the object) has not changed, and generates a proximity indication indicating a previous attachment state of the probe 105 (whether attached or detached, as the case may be).

With reference to FIG. 7E, in some embodiments, to generate the proximity indication in block 615, the probe controller 110 compares the capacitance of the circuit network 710e to a threshold amount. As noted with respect to block 610, the capacitance of the circuit network 710e for purposes of the process 600 is represented by, for example, the present value or an amount of change of the total capacitance of the circuit network 710e ($C_{TOT}$), capacitance of the proximity sensor 125e ($C_{SENSE}$), or the charge time ($T_{CHARGE}$) (which varies based on $C_{SENSE}$ and, thus, serves as a proxy thereof). When the comparison indicates that the capacitance of the circuit network 710e has increased more than a threshold amount, the probe controller 110 generates a proximity indication indicating that the probe 105 has become attached to the object to be monitored. When the comparison indicates that the capacitance of the resonant circuit network 710e has decreased more than a threshold amount, the probe controller 110 generates a proximity indication indicating that the probe 105 has become detached from the object to be monitored. When the comparison indicates that the capacitance of the resonant circuit network 710e has not increased or decreased more than a threshold amount, the probe controller 110 determines that the attachment state of the probe 105 (e.g., attached to or detached from the object) has not changed, and generates a proximity indication indicating a previous attachment state of the probe 105 (whether attached or detached, as the case may be).

As previously noted, in some embodiments of the circuit network 710e, an inductor is included in the proximity sensor 125e, rather than a conductor. In these embodiments, the probe controller 110 compares the inductance of the circuit network 710e to a threshold amount. The inductance of the circuit network 710e for purposes of the process 600 is represented by, for example, the present value or an amount of change of the total inductance of the circuit network 710e, an inductance of the proximity sensor 125e, or the charge time ($T_{CHARGE}$) (which varies based on inductance of the proximity sensor 125e and, thus, serves as a proxy thereof). When the comparison indicates that the inductance of the circuit network 710e has decreased more than a threshold amount, the probe controller 110 generates a proximity indication indicating that the probe 105 has become attached to the object to be monitored. When the comparison indicates that the capacitance of the resonant circuit network 710e has increased more than a threshold amount, the probe controller 110 generates a proximity indication indicating that the probe 105 has become detached from the object to be monitored. When the comparison indicates that the capacitance of the resonant circuit network 710e has not increased or decreased more than a threshold amount, the probe controller 110 determines that the attachment state of the probe 105 (e.g., attached to or detached from the object) has not changed, and generates a proximity indication indicating a previous attachment state of the probe 105 (whether attached or detached, as the case may be).

In some embodiments, the probe controller 110 determines the threshold amount used in block 615 based on a baseline value of capacitance or inductance for the circuit network 134 measured during a configuration step proceeding block 605. For example, the threshold amount may be a percentage of the baseline value. In some embodiments, the probe controller 110 uses a predetermined value as the threshold amount.

In some embodiments, the probe controller 110 may execute the process 600 repeatedly in a loop, whether as an independently looped process 600 (where the probe controller 110 returns to block 605 after block 615) or as part of the process 500 because the probe controller 110 loops back to repeatedly execute the block 505. For the network circuit 710e, where the probe controller 110 may excite the network circuit 710e with a constant current signal, before or when the probe controller 110 returns to block 605 after executing block 615, the probe controller 110 may interrupt the constant current signal. The interruption allows the capacitors (or inductor) of the circuit network 710e to discharge stored charge and the voltage signal (VC) 770 to decrease back to an initial level. Then, in block 605, the probe controller 110 may again generate the excitation signal (constant current signal). Accordingly, the excitation signal for the network circuit 710e may be periodic when the process 600 is looped.

In some embodiments, the probe controller 110 described with respect to process 600 of FIG. 6 and the diagrams 700a-e of FIGS. 7A-E includes the proximity controller 160 (see FIG. 1B), but not the biological sensor controller 165. In other words, the proximity controller 160 of the probe controller 110 may perform the process 600 and the functions of the probe controller 110 described with respect to diagrams 700a-e of FIGS. 7A-E.

Figure 8:
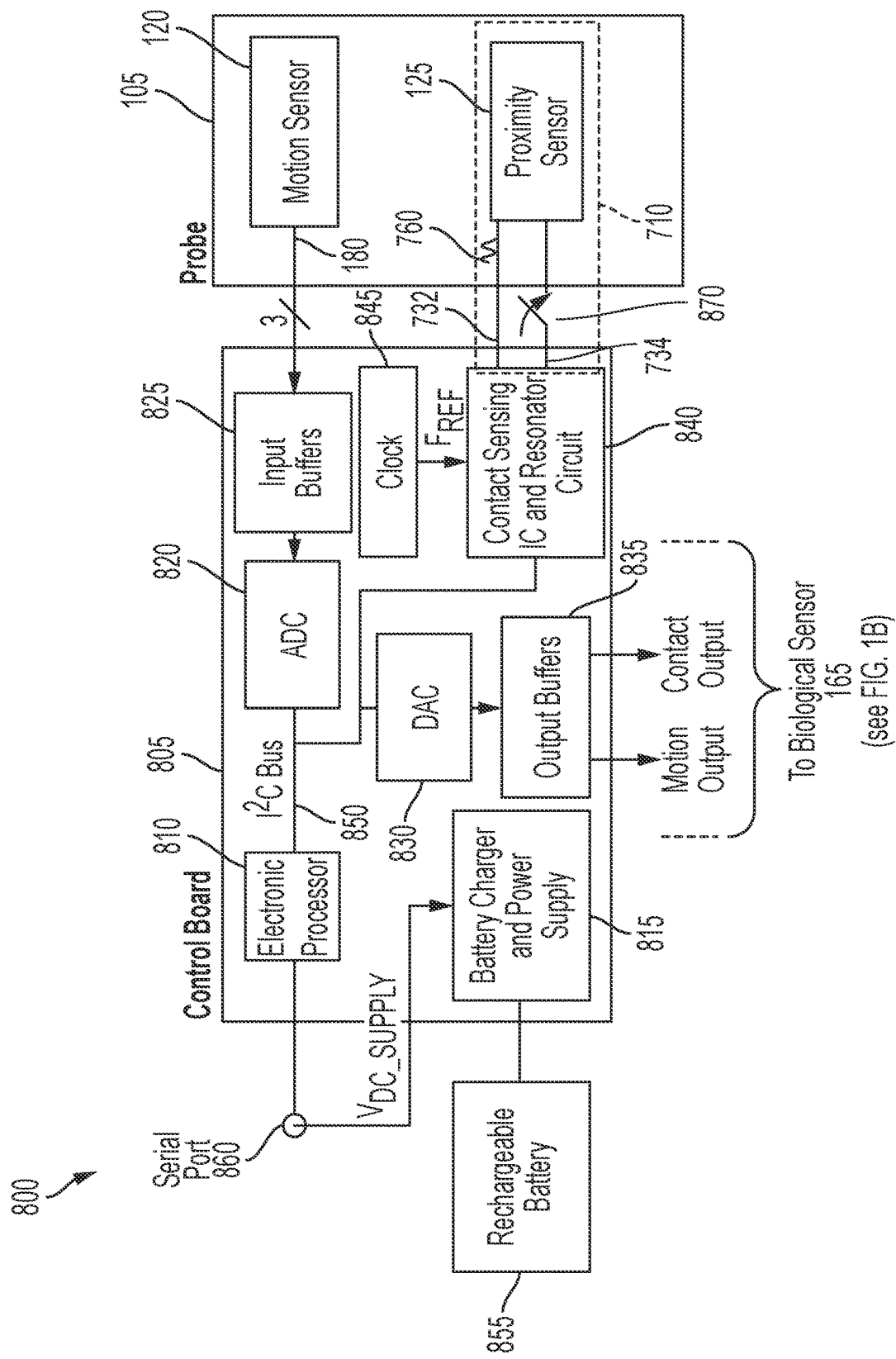
FIG. 8 illustrates an example of a proximity controller of the sensor assembly of FIGS. 1B, according to some embodiments.

FIG. 8 illustrates a proximity controller 800, which is an example of the proximity controller 160. In some embodiments, the proximity controller 160 has fewer or more components than the proximity controller 800 shown in FIG. 8, and/or a different arrangement of components.

In FIG. 8, the proximity controller 800 includes a control board 805, which may be a printed circuit board. The control board 805 includes thereon an electronic processor 810, a battery charger and power supply 815, an analog-to-digital converter (ADC) 820, input buffers 825, a digital-to-analog converter (DAC) 830, output buffers 835, contact sensing integrated circuit and resonator circuit 840, and a clock 845. The electronic processor 810, ADC 820, DAC 830, and contact sensing IC and resonant circuit 840 may be coupled by, and communicate via, a communication bus 850. The battery charger and power supply 815 is configured to provide power to the components of the control board 805. The battery charger and power supply 815 may be coupled to an external rechargeable battery 855 and/or a serial port 860 (e.g., a USB 2.0 port or similar port), each of which may provide a voltage supply (e.g., a direct current (DC) voltage supply). The serial port 860 may be selectively coupled to an external computing device (e.g., a laptop, desktop computer, tablet, etc.) to program and control the electronic processor 810, and/or to provide the voltage supply to the battery charger and power supply 815. In addition to powering the other components of the control board 805, the battery charger and power supply 815 is configured to use the voltage supply to charge the rechargeable battery 855.

The electronic processor 810 is, for example, an 8-bit microcontroller including a processor, memory, and I/O interface (e.g., similar to the components described with respect to the probe controller 110 of FIG. 1A). The electronic processor 810 is configured to communicate with and control the other components of the control board 805 via the bus 850. The electronic processor 810 may also store motion data received from the ADC 820 and proximity sensor data from the contact sensing IC and resonator circuit 840 (e.g., for later retrieval by the external computing device via the serial port 860).

The input buffers 825 are coupled to the motion sensor wires 180 of the motion sensor 120, which may include three wires sending respective signals for each of the x, y, and z directions in which motion is sensed. Accordingly, the input buffers 825 may receive analog motion data (e.g., acceleration or gyroscopic data) including three signals: a first signal indicating motion in the x-direction, a second signal indicating motion in the y-direction, and a third signal indicating motion in the z-direction. The input buffers 825 buffer these signals and provide the buffered motion signals to the ADC 820, which converts the analog motion signals to digital motion signals. In some embodiments, the motion signals are combined (e.g., the absolute values of the motion signals are summed) to form a single motion signal. The motion signals may be combined in hardware that is part of the input buffers 825 or the ADC 820, or the electronic processor 810 may receive the digital motion signals from the ADC 820 and combine them into the motion signal. In some embodiments, the motion sensor 120 outputs the motion data in digital form, rather than analog form, and the ADC 820 is not included in the proximity controller 800.

The motion signal is provided to the DAC 830, which converts the digital motion signal to an analog motion signal and provides the analog motion signal to the output buffers 835. The output buffers 835 then output the motion signal (e.g., to the biological sensor controller 165 of FIG. 1B). In some embodiments, rather than providing the raw motion signal, the electronic processor 810 analyzes the motion data and determines whether excessive motion is being experienced by the probe 105 (see, e.g., block 510 of FIG. 5). The digital motion signal output by the electronic processor 810 to the DAC 830 for output via the output buffers 835, in turn, is an indication of whether excessive motion is being experienced by the probe 105.

The contact sensing IC and resonator circuit 840 (also referred to as the resonator circuit 840) is configured to excite a resonant network including the proximity sensor 125 and measure a frequency of an oscillating signal on the resonant network to determine whether the proximity sensor 125 indicates that the probe 105 is attached to an object to be monitored. The resonant network and proximity sensor may be configured, for example, according to one of the diagrams 700a-d of FIGS. 7A-D. As described with reference to FIGS. 7A-D, the resonant networks 710a-d may include the associated proximity sensor 125a-d as well as the circuit elements 715a-d. The circuit elements 715a-d including a tank capacitor 720, an inductor capacitor 725, and one or more stray capacitances 730. Turning to FIG. 8, one of the resonant networks 710a-d, identified in FIG. 8 as a resonant network 710, may be formed from components of the resonator circuit 840, the proximity sensor 125, and the connecting wires of the nodes 732 and 734. More particularly, the tank capacitor 720 and inductor capacitor 725 may be part of the resonator circuit 840 and the stray capacitances 730 are attributes of the nodes 732 and 734.

The resonator circuit 840 receives a clock signal $F_{REF}$ from the clock 845 and uses the clock signal to generate the excitation signal (see block 605 of FIG. 6) at the nodes 732 and 734 of the resonant network 710. The resonator circuit 840 further monitors the nodes 732 and 734 to determine a frequency of the oscillating signal 760 resulting from the excitation signal on the resonant network 810 (see block 610 of FIG. 6). The resonator circuit 840 outputs the determined frequency as a digital signal on the communication bus to the electronic processor 810. The electronic processor 810 then generates the proximity indication based on the determined frequency (see block 615 of FIG. 6). The electronic processor 810 provides the (digital) proximity indication to the DAC 830, which converts the proximity indication to an analog signal. In some embodiments, the electronic processor 810 applies a gain (negative or positive) and/or baseline offset to the signal before providing it to the DAC 830 to accommodate the characteristics of the DAC 830 (e.g., number of bits) and to improve utilization of the operating range of the DAC 830 (e.g., to provide sufficient information to be conveyed about frequency shifts from increases and decreases without increasing the size of the DAC 830). The DAC 830 then provides the analog proximity indication to the output buffers 835. The output buffers 835 then output the proximity indication (e.g., to the biological sensor controller 165 of FIG. 1B).

In some embodiments, a switch 870, which may be on the control board 805 or external to the control board 805, is selectively controlled by the electronic processor 810 or the resonator circuit 840 to connect the node 734 to the proximity sensor 125. In some embodiments, the node 734 may be disconnected from the proximity sensor 125. For example, the switch 870 may be controlled to disconnect the node 734 from the proximity sensor 125 for embodiments of the circuit network 710a of FIG. 7A that do not include an additional wire connected to a dummy terminal to compensate for stray capacitance. In some embodiments, the switch 870 is controlled to connect the node 734 to the proximity sensor 125 (e.g., for the circuit networks 710b-e and the circuit network 710a when the additional wire is to be connected to the dummy terminal).

Figure 9:
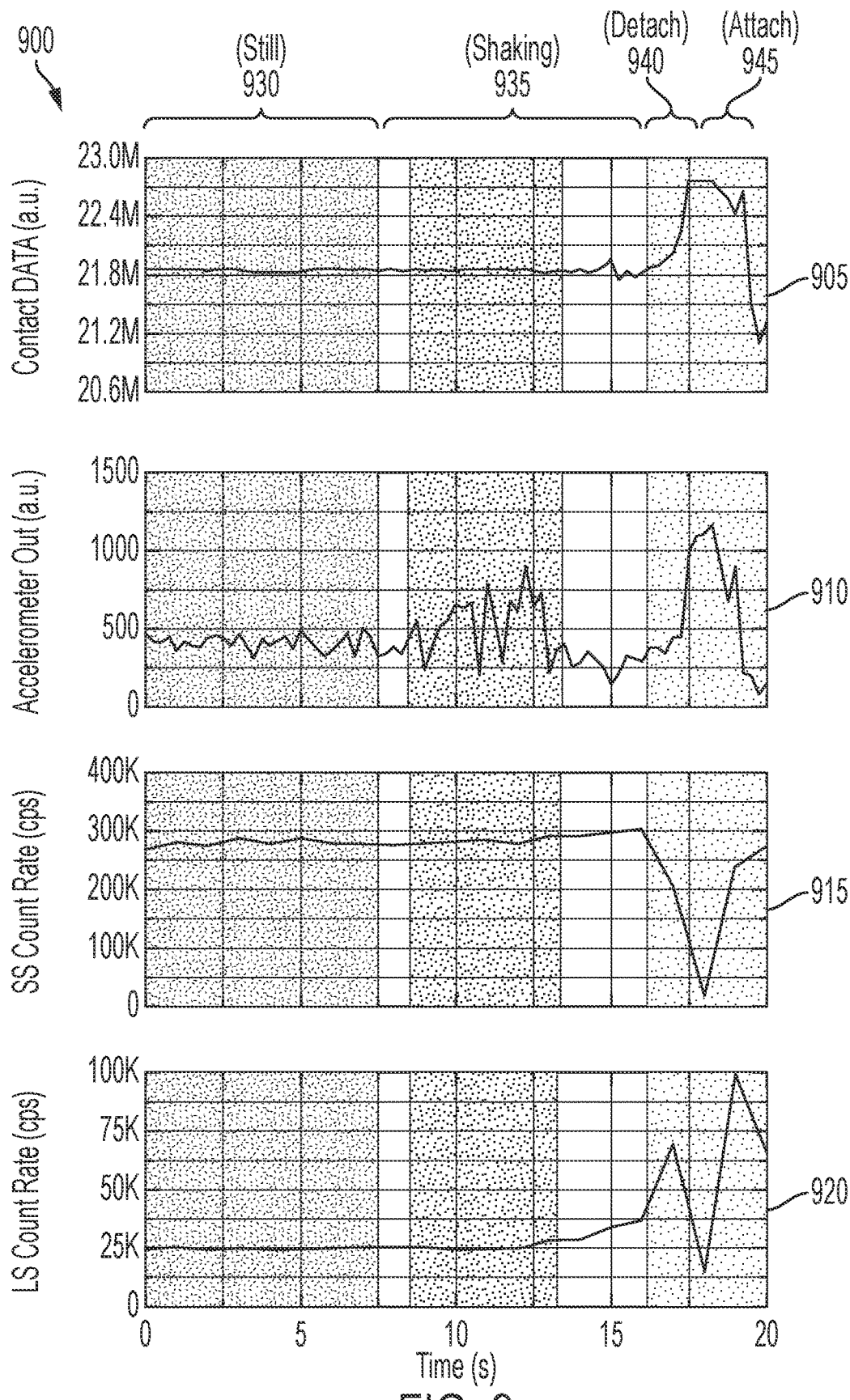
FIG. 9 illustrates sensor data plots having sensor data generated by the probe of the sensor assembly of FIGS. 1A-B, according to some embodiments.

FIG. 9 illustrates example sensor data plots 900 having sensor data generated by the probe 105 of the sensor assembly 100 placed on the forehead of a human patient. As illustrated in FIGS. 1A-B, the probe 105 generating the sensor data includes the motion sensor 120, the proximity sensor 125, and the biological sensor 130. In the embodiment of the probe 105 generating the sensor data of FIG. 9, the proximity sensor 125 is a capacitive proximity sensor that is part of a resonant network, such as the proximity sensors 125a, 125b, or 125c (of FIGS. 7A-C). Additionally, the biological sensor 130 is a diffuse correlation spectroscopy (DCS) sensor that includes a laser transmitter, a reference photo detector, and a sample photo detector.

The sensor data plots of FIG. 9 include a proximity data plot 905, an acceleration data plot 910, an SS count rate plot 915, and an LS count rate plot 920. Each of the sensor data plots includes time-series sensor data collected over a time period of 20 seconds (s). The time period includes four segments: a first segment 930 in which the probe 105 is attached to the patient and the patient is still; a second segment 935 in which the probe 105 is attached to the patient and the patient's head is shaking; a third segment 940 in which the probe 105 is detached from the patient; and a fourth segment 945 in which the probe 105 is reattached to the patient.

The proximity data plot 905 has a y-axis indicating a frequency of an oscillating signal of the resonant network incorporating the proximity sensor 125, such as the oscillating signal 760 of FIGS. 7A-C. As shown, the oscillating signal has a frequency of approximately 21.8 megahertz (MHz) until detachment of the probe 105 in the third segment 940, at which point the oscillating signal increases to above 22.4 MHz. As described with respect to FIGS. 6-7C, the increase is due to the decreased capacitance of the proximity sensor 125 upon detaching of the probe 105 from the patient's forehead. Upon reattachment of the probe 105 in the fourth segment 945, the oscillating signal decreases. As described with respect to FIGS. 6-7C, the decrease is due to the increased capacitance of the proximity sensor 125 upon attaching of the probe 105 to the patient's forehead.

The acceleration data plot 910 has a y-axis indicating the acceleration experienced by the motion sensor 120 of the proximity sensor 125. As shown, the acceleration is low and has low fluctuation in the first stage 930, has increased fluctuation during the second stage 935, third stage 940, and fourth stage 945.

The LS count rate plot 920 corresponds to an output of the sample sensor of the biological sensor 130 (e.g., indicating brain blood flow, but may have additional noise from skin blood flow) and the SS count rate plot 915 corresponds to an output of a reference sensor of the biological sensor 130 (e.g., used to detect background noise (e.g., caused by skin blood flow) as a reference signal to subtract from the sample sensor data). The SS count rate plot 915 has a y-axis indicating the (photon) counts per second (cps) experienced by the reference sensor, and the LS count rate plot 920 has a y-axis indicating the (photon) counts per second (cps) experienced by the sample sensor. In other embodiments, the LS count may be used as a reference and the SS count may be used as sample data. In some embodiments, the biological sensor incorporated or secured to the probe 105 includes more than one light source and/or more than two detection points (e.g., photo detectors) or only one detection point.

As shown, the SS count rate and LS count rate experience low fluctuations in the first stage 930 and the second stage 935, and increased fluctuation during the third stage 940 and fourth stage 945.

Figure 10:
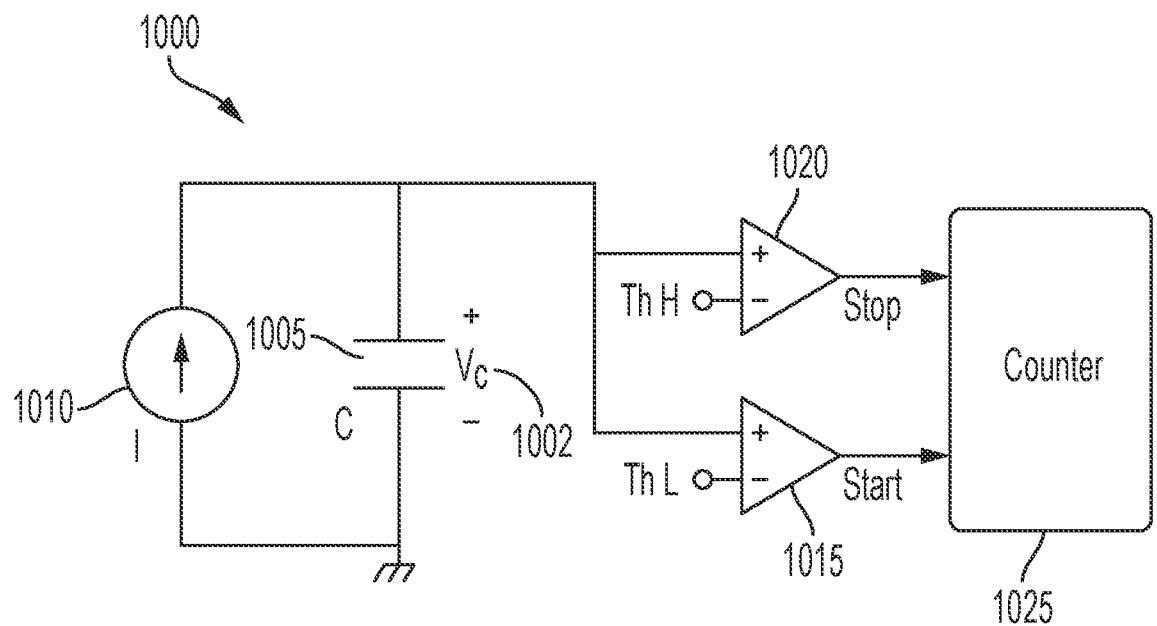
FIG. 10 illustrates a circuit for determining a charge time for a voltage signal on a capacitive circuit network, according to some embodiments.

FIG. 10 illustrates a circuit 1000 that may be used to determine a charge time ($T_{CHARGE}$) for a voltage signal ($V_C$) 1002 on a capacitive circuit network 1005 to reach a charged level. The circuit 1000 may be used with respect to the circuit network 710e of FIG. 0.7E. For example, the capacitive circuit network 1005 may represent the total capacitance of the circuit network 710e (e.g., including the stray capacitances 730 and the capacitance 735 of the proximity sensor 125e). Thus, the voltage signal ($V_C$) 1002 equates to the voltage signal ($V_C$) 770 of FIG. 7E. The circuit 1000 includes a current source 1010, a start comparator 1015, a stop comparator 1020, and a counter 1025. The current source 1010 is configured to generate a constant current. The current charges the capacitive circuit network 1005, increasing the voltage signal ($V_C$) 1002. When the voltage signal ($V_C$) 1002 reaches a first threshold (Th L), the comparator 1015 outputs a start signal to the counter 1025. The counter 1025, which may be a clocked counter that receives a clock reference signal and can be used to track time, starts counting (e.g., incrementing a counter) in response to the start signal. As the current continues to charge the capacitive circuit network 1005, the voltage signal ($V_C$) 1002 continues to increase. When the voltage signal ($V_C$) 1002 reaches the second threshold (Th H), the comparator 1020 outputs a stop signal to the counter 1025. The counter 1025 stops counting in response to the stop signal. The value of the counter 1025 indicates the charge time ($T_{CHARGE}$) for the voltage signal ($V_C$) 1002 on the capacitive circuit network 1005. When the capacitance of the capacitive circuit network 1005 increases (e.g., because the proximity sensor 125e touches an object), the charge time ($T_{CHARGE}$) increases. When the capacitance of the capacitive circuit network 1005 decreases (e.g., because the proximity sensor 125e detaches from an object), the charge time ($T_{CHARGE}$) decreases. Accordingly, the charge time indicates the capacitance of the capacitive circuit network 1005 and, in turn, whether the proximity sensor 125e is attached to an object to be monitored. The current source 1010 may be periodically interrupted to allow time for the capacitive circuit network 1005 to discharge, bringing the voltage signal ($V_C$) 1002 back down below the first threshold (Th L), and then the current source 1010 may again provide a constant current so that the charge time ($T_{CHARGE}$) may again be measured and the capacitance of the capacitive circuit network 1005 determined.

In some embodiments, the probe controller 110 implements the circuit 1000, including controlling the current source 1010 to periodically generate the constant current and analyzing the counter values provided by the counter 1025. Accordingly, the probe controller 110 may use the circuit 1000 to implement the process 600, in some embodiments (e.g., when the circuit network 134 takes the form of the circuit network 710e of FIG. 7E).

Figure 11:
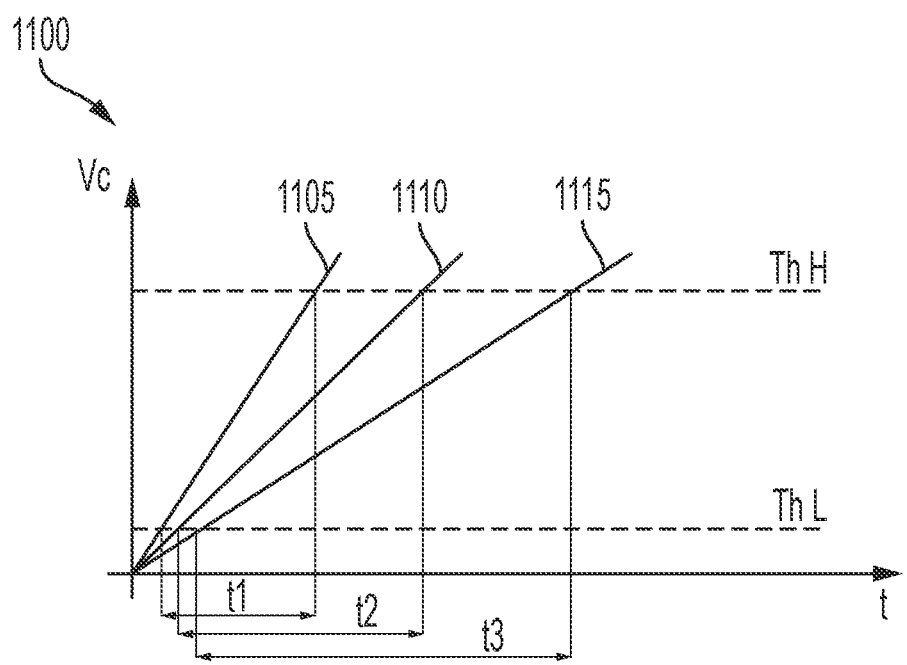
FIG. 11 illustrates a charge time data plot including charge time data generated by the circuit of FIG. 10.

FIG. 11 illustrates a charge time data plot 1100 including charge time data generated by the circuit 1000. The charge time data plot 1100 plots voltage (of the voltage signal (VC) 1002 on the y-axis against time on the x-axis, and illustrates the low threshold (Th L) and the high threshold (Th H) of the comparators 1015 and 1020, respectively. The charge time data plot 1100 includes three charge time plots 1105, 1110, and 1115, each associated with a different capacitance of the capacitive circuit network 1005. The charge time plot 1105 has the shortest charge time ($T_{CHARGE}=t_1$), the charge time plot 1115 has the longest charge time ($T_{CHARGE}=t_3$), and the charge time plot 1110 has a charge time ($T_{CHARGE}=t_2$) that is between the charge time $t_1$ and $t_3$. Accordingly, the charge time plot 1105 is associated with the lowest capacitance of the capacitive circuit network 1005, the charge time plot 1115 is associated with the highest capacitance of the capacitive circuit network 1005, and the charge time plot 1110 is associated with a capacitance that is between the low and high capacitances associated with the charge time plots 1105 and 1115, respectively.

Thus, while particular embodiments and examples have been provided above, numerous other embodiments, examples, uses, modifications and departures from the embodiments, examples and uses are intended to be encompassed by the claims attached hereto.

What is claimed is:

1. A sensor assembly comprising:
   a probe including a printed circuit board substrate having a sensing side and a back side opposite the sensing side, the sensing side having:
     a proximity sensor having a passive energy storing circuit element, and
     a biological sensor receptacle configured to receive a biological sensor for sensing a biological characteristic of an object that engages the sensing side; and
   an electronic probe controller coupled the probe and configured to:
     excite a circuit network incorporating the proximity sensor with an excitation signal,
     determine a characteristic of the circuit network that is excited by the excitation signal, and
     generate a proximity indication indicating a probe attachment state based on the characteristic of the circuit network.

2. The sensor assembly of claim 1, wherein the circuit network is a resonant network and the passive energy storing circuit element includes a first conductor of a capacitor.

3. The sensor assembly of claim 2, wherein the proximity sensor includes a second conductor of the capacitor.

4. The sensor assembly of claim 2,
   wherein the characteristic of the resonant network is a capacitance of the resonant network; and
   wherein, to generate the proximity indication based on the characteristic, the electronic probe controller is configured to:
     determine whether the capacitance of the resonant network has changed above a threshold amount, and
     generate the proximity indication in response to determining whether the capacitance of the resonant network has changed above the threshold amount.

5. The sensor assembly of claim 1, wherein, to determine the characteristic of the circuit network, the electronic probe controller is configured to determine a capacitance of the circuit network, wherein the capacitance is represented by at least one selected from the group of:
   a total capacitance of the resonant circuit network,
   a capacitance of the proximity sensor,
   a frequency of an oscillating signal of the resonant circuit network, and
   a charge time of the proximity sensor.

6. The sensor assembly of claim 1, wherein, to determine the characteristic of the circuit network, the electronic probe controller is configured to determine an inductance of the circuit network, where the inductance is represented by at least one selected from the group of:
   a total inductance of the resonant circuit network,
   an inductance of the proximity sensor, and
   a frequency of an oscillating signal of the resonant circuit network.

7. The sensor assembly of claim 1,
   wherein the printed circuit board substrate is a flexible printed circuit board,
   wherein the sensing side is configured to engage the object,
   wherein the passive energy storing circuit element is positioned on the sensing side, and
   wherein a dielectric coating is on the passive energy storing circuit element.

8. The sensor assembly of claim 7,
   wherein the probe further includes:
     a motion sensor positioned on the back side; and
   wherein the controller is further configured to:
     receive an output from the motion sensor, and
     generate a movement indication indicating an amount of movement of the probe.

9. The sensor assembly of claim 8, wherein the electronic probe controller is further configured to:
   receive, from the biological sensor coupled to the biological sensor receptacle, a signal indicative of the biological characteristic of the object, wherein receiving the signal is in response to the probe attachment state and the movement indication indicating the amount of movement of the probe being below a motion threshold.

10. The sensor assembly of claim 1, further comprising:
    the biological sensor coupled to the biological sensor receptacle, the biological sensor configured to provide a signal indicative of the biological characteristic of the object.

11. The sensor assembly of claim 1, wherein the probe attachment state is at least one selected from the group of:
    an attached state in which the probe is attached to the object,
    a detached state in which the probe is detached from the object, and
    an attachment level indicator indicating a quality of attachment of the probe to the object.

12. A sensor assembly comprising:
    a probe including
      a proximity sensor having a passive energy storing circuit element, and
      a biological sensor receptacle configured to receive a biological sensor for sensing a biological characteristic of an object; and
    an electronic probe controller coupled the probe and configured to:
      excite a circuit network incorporating the proximity sensor with an excitation signal,
      determine a characteristic of the circuit network that is excited by the excitation signal, and
      generate a proximity indication indicating a probe attachment state based on the characteristic of the circuit network,
    wherein the circuit network is a resonant network and wherein the passive energy storing circuit element includes an inductor, wherein the characteristic of the resonant network is an inductance of the resonant network; and wherein, to generate the proximity indication based on the characteristic, the electronic probe controller is configured to:

determine whether the inductance of the resonant network has changed above a threshold amount, and generate the proximity indication in response to determining whether the inductance of the resonant network has changed above the threshold amount.

13. A method of sensing probe proximity comprising:

exciting a circuit network incorporating a proximity sensor with an excitation signal, the proximity sensor having a passive energy storing circuit element and being incorporated into a probe with a biological sensor receptacle;

determining a characteristic of the circuit network that is excited by the excitation signal;

generating a proximity indication indicating a probe attachment state based on the characteristic of the circuit network;

receiving an output from a motion sensor of the probe;

generating a movement indication indicating an amount of movement of the probe; and receiving, from a biological sensor coupled to the biological sensor receptacle, a signal indicative of a biological characteristic of the object in response to the probe attachment state and the movement indication indicating the amount of movement of the probe being below a motion threshold.

14. The method of claim 13, wherein the circuit network is a resonant network and the passive energy storing circuit element includes a first conductor of a capacitor.

15. The method of claim 14, wherein the proximity sensor includes a second conductor of the capacitor.

16. The method of claim 14, wherein the characteristic of the resonant network is a capacitance of the resonant network and wherein generating the proximity indication based on the characteristic includes:

determining whether the capacitance of the resonant network has changed above a threshold amount, and generating the proximity indication in response to determining whether the capacitance of the resonant network has changed above the threshold amount.

17. The method of claim 13, wherein the circuit network is a resonant network and wherein the passive energy storing circuit element includes an inductor.

18. The method of claim 17, wherein the characteristic of the resonant network is an inductance of the resonant network and wherein generating the proximity indication based on the characteristic includes:

determining whether the inductance of the resonant network has changed above a threshold amount, and generating the proximity indication in response to determining whether the inductance of the resonant network has changed above the threshold amount.

19. The method of claim 13, wherein determining a characteristic of the circuit network that is excited by the excitation signal includes at least one selected from the group of:

determining a capacitance of the circuit network, wherein the capacitance is represented by at least one selected from the group of:

a total capacitance of the resonant circuit network, a capacitance of the proximity sensor, a frequency of an oscillating signal of the resonant circuit network, and a charge time of the proximity sensor; and determining an inductance of the circuit network, wherein the inductance is represented by at least one selected from the group of:

a total inductance of the resonant circuit network, an inductance of the proximity sensor, and a frequency of an oscillating signal of the resonant circuit network.

20. The method of claim 13, further comprising:

determining a further probe attachment state based on further exciting the circuit network incorporating the proximity sensor;

determining a further amount of movement of the probe based on further output from the motion sensor; and ceasing receiving of the signal from the biological senor in response to one or more of the further probe attachment state indicting probe detachment, or the further amount of movement of the probe indicating excessive movement.

\* \* \* \* \*